US008110329B2

(12) United States Patent
Tominaga et al.

(10) Patent No.: US 8,110,329 B2
(45) Date of Patent: Feb. 7, 2012

(54) CHARGE CONTROLLING AGENT AND TONER

(75) Inventors: Akiko Tominaga, Kawasaki (JP); Tatsuki Fukui, Yokohama (JP); Takashi Kenmoku, Mishima (JP); Ako Kusakari, Tokyo (JP); Masato Minami, Yokohama (JP); Tetsuya Yano, Tokyo (JP); Takeshi Ikeda, Shizuoka-Ken (JP); Norikazu Fujimoto, Susono (JP); Atsushi Tani, Shizuoka-Ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 1139 days.

(21) Appl. No.: 11/557,823

(22) Filed: Nov. 8, 2006

(65) Prior Publication Data

US 2007/0111125 A1    May 17, 2007

(30) Foreign Application Priority Data

Nov. 11, 2005  (JP) .................................. 2005-328210

(51) Int. Cl.
    *G03G 9/087*    (2006.01)
(52) U.S. Cl. .................. 430/108.2; 430/108.1; 564/162; 564/192
(58) Field of Classification Search ............... 430/108.1, 430/108.2; 564/162, 192
    See application file for complete search history.

(56) References Cited

U.S. PATENT DOCUMENTS

| 5,510,379 A | * | 4/1996 | Lee et al. .................. 514/517 |
| 5,679,491 A | * | 10/1997 | Oshiba et al. ............. 430/108.2 |
| 5,759,247 A | * | 6/1998 | Gregory et al. ........... 430/108.21 |
| 2005/0084786 A1 | | 4/2005 | Kuroda et al. |
| 2005/0096385 A1 | * | 5/2005 | Kong et al. .................... 514/464 |
| 2005/0287463 A1 | | 12/2005 | Fukui et al. |
| 2005/0287484 A1 | | 12/2005 | Yano et al. |
| 2006/0014921 A1 | | 1/2006 | Mihara et al. |
| 2006/0035098 A1 | | 2/2006 | Fukui et al. |
| 2007/0059627 A1 | | 3/2007 | Fukui et al. |

FOREIGN PATENT DOCUMENTS

JP    11-084733    *    3/1999

OTHER PUBLICATIONS

Translation of JP 11-084733 published Mar. 1999.*
Patent Abstract for JP 2005-121776, Kuroda Kazuyoshi, et al (May 12, 2005).
Allan K. Colter, et al., "Reactions of 2-Pentyl Arenesulfonates with Ethanolic Sodium Ethoxide. A Study of Electronic Effects in the E2 Reaction", J.A.C.S., vol. 84, pp. 3289-3295 (1962).
Sergio Thea, et al.,"Catalysis of Sulfonate Ester Hydrolysis by Intramolecular Amide Group Assistance", J. Org. Chem. vol. 50, pp. 3336-3341 (1985).

* cited by examiner

*Primary Examiner* — Peter Vajda
(74) *Attorney, Agent, or Firm* — Fitzpatrick, Cella, Harper & Scinto

(57) ABSTRACT

A charge controlling agent is provided as a compound in which an amide group is introduced together with a sulfonic group or a derivative thereof. The charge controlling agent is characterized by including at least one compound represented by the chemical formula (2) in which an amide group is introduced together with at least one of a sulfonic group, a sulfonic acid ester, a sulfonic acid salt, and a sulfonic acid halide.

1 Claim, 5 Drawing Sheets

CHARGE CONTROLLING AGENT AND TONER

BACKGROUND OF THE INVENTION

1. Field of the Invention

The present invention relates to a charge controlling agent and a toner.

2. Description of the Related Art

In general, sulfonic groups have been used as pharmaceutical agents and sulfonic acid derivative groups have been used as surfactants or resist materials.

A compound that contains a sulfonic group or a sulfonic acid derivative group has been expected to be applied in various applications.

In addition, the compound has been also expected to be used as a charge controlling agent. In Japanese Patent Application Laid-Open No. 2005-121776, for example, a method of manufacturing a charge controlling agent that contains an azo-containing metal complex is described, in which a metal-containing compound is used as a charge controlling agent in a toner having a negative static charge property.

SUMMARY OF THE INVENTION

Compounds containing sulfonic groups and sulfonic acid derivatives have been expected to be applied in various applications. However, known materials for such compounds may not be sufficient. Therefore, provisions of further improvements and a novel structure have been desired.

Consequently, an object of the present invention is to provide a novel charge controlling agent that utilizes a compound containing a sulfonic group or a derivative thereof and to provide a toner for developing an electrostatic charge containing the novel charge controlling agent.

In consideration of the above-mentioned related art, the inventors of the present invention have made an intensive study for creating various useful compounds which do not contain any metal as a charge controlling agent, and have finally attained the present invention.

According to an aspect of the present invention, there is provided a charge controlling agent, including at least one compounds represented by the chemical formula (2):

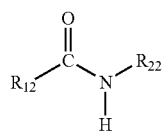

(2)

in which $R_{12}$ and $R_{22}$ satisfy the following conditions (1) to (4);

(1) $R_{12}$ and $R_{22}$ independently represent any one of a substituted or unsubstituted aliphatic hydrocarbon structure, a substituted or unsubstituted aromatic ring structure, and a substituted or unsubstituted heterocyclic structure;

(2) at least one of $R_{12}$ and $R_{22}$ has at least one $SO_2R_{32}$ group as a substituent;

(3) $R_{32}$ represents OH, a halogen atom, ONa, OK, or $OR_{42}$; and (4) $R_{42}$ represents any one of a substituted or unsubstituted aliphatic hydrocarbon structure, a substituted or unsubstituted aromatic ring structure, and a substituted or unsubstituted heterocyclic structure.

In addition, according to another aspect of the present invention, there is provided a toner for developing an electrostatic charge image, including at least:
a binder resin;
a coloring agent; and
a charge controlling agent having a structure represented by the chemical formula (2).

In addition, according to another aspect of the present invention, there is provided a toner for developing an electrostatic charge, including:
a binder resin;
a coloring agent; and
a compound represented by the chemical formula (2):

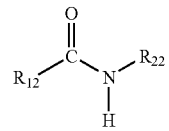

(2)

in which $R_{12}$ and $R_{22}$ satisfy the following conditions (1) to (4);

(1) $R_{12}$ and $R_{22}$ independently represent any one of a substituted or unsubstituted aliphatic hydrocarbon structure, a substituted or unsubstituted aromatic ring structure, and a substituted or unsubstituted heterocyclic structure;

(2) at least one of $R_{12}$ and $R_{22}$ contains at least one $SO_2R_{32}$ group as a substituent;

(3) $R_{32}$ represents OH, a halogen atom, ONa, OK, or $OR_{42}$; and (4) $R_{42}$ represents any one of a substituted or unsubstituted aliphatic hydrocarbon structure, a substituted or unsubstituted aromatic ring structure, and a substituted or unsubstituted heterocyclic structure.

Consequently, the present invention provides a charge controlling agent and a toner for developing an electrostatic charge image, containing the charge controlling agent.

Further features of the present invention will become apparent from the following description of exemplary embodiments with reference to the attached drawings.

DESCRIPTION OF THE EMBODIMENTS

Figure 1:
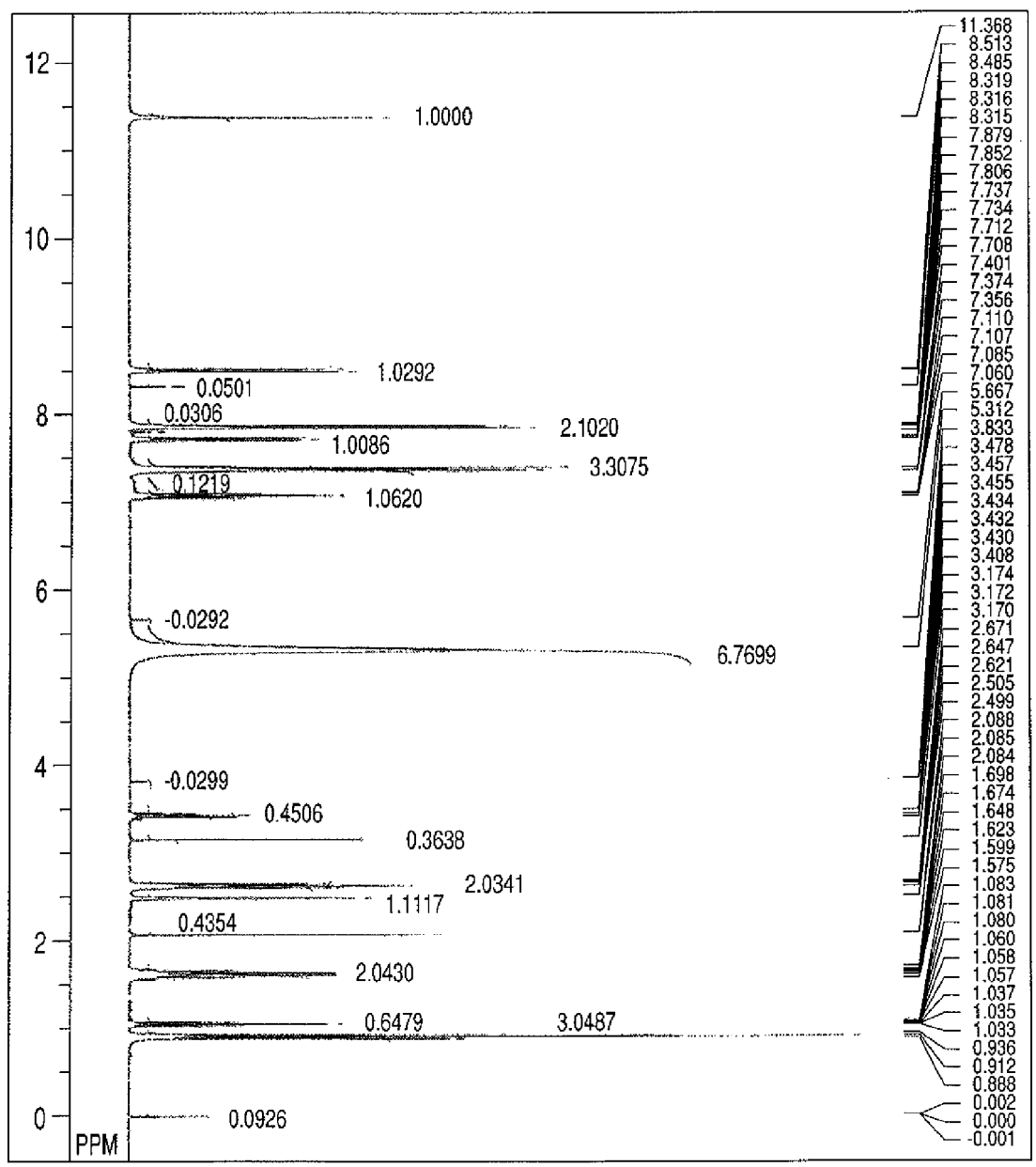
FIG. 1 illustrates the results of $^1$H-NMR measurement of the exemplified compound B-1.

Next, preferable embodiments of the present invention will be described in detail.

The charge controlling agent of the present invention contains a compound in which an amide group and at least one of a sulfonic group and a derivative thereof (e.g., a sulfonic acid ester, a sulfonic acid salt, or a sulfonic acid halide) are introduced. Preferable embodiments include the following (1) to (8).

<1> According to a first aspect of the present invention, there is provided a charge controlling agent, including at least one compounds represented by the chemical formula (2):

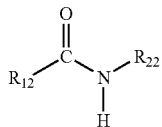

(2)

in which $R_{12}$ and $R_{22}$ satisfy the following conditions (1) to (4);

(1) $R_{12}$ and $R_{22}$ independently represent any one of a substituted or unsubstituted aliphatic hydrocarbon structure, a substituted or unsubstituted aromatic ring structure, and a substituted or unsubstituted heterocyclic structure;

(2) at least one of $R_{12}$ and $R_{22}$ has at least one $SO_2R_{32}$ group as a substituent;

(3) $R_{32}$ represents OH, a halogen atom, ONa, OK, or $OR_{42}$; and (4) $R_{42}$ represents any one of a substituted or unsubstituted aliphatic hydrocarbon structure, a substituted or unsubstituted aromatic ring structure, and a substituted or unsubstituted heterocyclic structure.

<2> According to a second aspect of the present invention, there is provided a charge controlling agent, including at least one of compounds each of which has the structure represented by the chemical formula (2) and satisfies the following conditions (1) to (4):

(1) $R_{12}$ and $R_{22}$ independently represent any one of a substituted or unsubstituted aliphatic hydrocarbon structure and a substituted or unsubstituted aromatic ring structure;

(2) at least one of $R_{12}$ and $R_{22}$ has at least one $SO_2R_{32}$ group as a substituent;

(3) $R_{32}$ represents OH, a halogen atom, ONa, OK, or $OR_{42}$; and (4) $R_{42}$ represents any one of a substituted or unsubstituted alkyl group having 1 to 18 carbon atoms, a substituted or unsubstituted phenyl group, and a substituted or unsubstituted naphthyl group.

<3> According to a third aspect of the present invention, there is provided a charge controlling agent, including at least one of compounds each of which has the structure represented by the chemical formula (2) and satisfy at least one of the following conditions (1) and (2):

(1) the chemical formula (2) has a structure represented by the chemical formula (21) and satisfies the following conditions (i) to (iv):

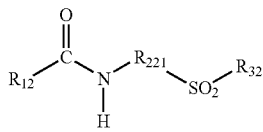

(21)

(i) $R_{12}$ represents any one of a substituted or unsubstituted alkyl group having 1 to 18 carbon atoms, a substituted or unsubstituted phenyl group, and a substituted or unsubstituted naphthyl group;

(ii) $R_{221}$ represents any one of a substituted or unsubstituted aliphatic hydrocarbon structure and a substituted or unsubstituted aromatic ring structure;

(iii) $R_{32}$ represents OH, a halogen atom, ONa, OK, or $OR_{42}$; and (iv) $R_{42}$ represents any one of a substituted or unsubstituted alkyl group having 1 to 18 carbon atoms, a substituted or unsubstituted phenyl group, and a substituted or unsubstituted naphthyl group; and (2) the chemical formula (2) has a structure represented by the chemical formula (22) and satisfies the following conditions (i) to (iv):

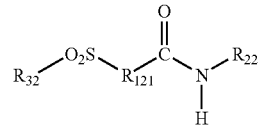

(22)

(i) $R_{121}$ represents any one of a substituted or unsubstituted aliphatic hydrocarbon structure and a substituted or unsubstituted aromatic ring structure;

(ii) $R_{22}$ represents any one of a substituted or unsubstituted alkyl group having 1 to 18 carbon atoms, a substituted or unsubstituted phenyl group, and a substituted or unsubstituted naphthyl group;

(iii) $R_{32}$ represents OH, a halogen atom, ONa, OK, or $OR_{42}$; and (iv) $R_{42}$ represents any one of a substituted or unsubstituted alkyl group having 1 to 18 carbon atoms, a substituted or unsubstituted phenyl group, and a substituted or unsubstituted naphthyl group.

<4> According to a fourth aspect of the present invention, there is provided a charge controlling agent, including at least one of compounds each of which has the structure represented by the chemical formula (2) and satisfies at least one of the following conditions (3) and (4);

(3) the chemical formula (2) has a structure represented by the chemical formula (23) and satisfies the following conditions (i) to (iv):

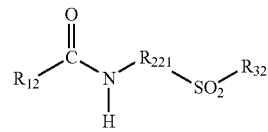

(23)

(i) $R_{12}$ represents any one of a substituted or unsubstituted aliphatic hydrocarbon structure and a substituted or unsubstituted aromatic ring structure;

(ii) $R_{221}$ represents any one of a substituted or unsubstituted alkyl group having 1 to 18 carbon atoms, a substituted or unsubstituted phenyl group, and a substituted or unsubstituted naphthyl group;

(iii) $R_{32}$ represents OH, a halogen atom, ONa, OK, or $OR_{42}$; and (iv) $R_{42}$ represents any one of a substituted or unsubstituted alkyl group having 1 to 18 carbon atoms, a substituted or unsubstituted phenyl group, and a substituted or unsubstituted naphthyl group; and (4) the chemical formula (2) has a structure represented by the chemical formula (24) and satisfies the following conditions (i) to (iv):

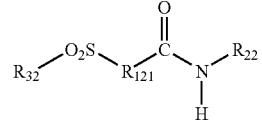

(24)

(i) $R_{121}$ represents any one of a substituted or unsubstituted alkyl group having 1 to 18 carbon atoms, a substituted or unsubstituted phenyl group, and a substituted or unsubstituted naphthyl group;

(ii) $R_{22}$ represents any one of a substituted or unsubstituted aliphatic hydrocarbon structure and a substituted or unsubstituted aromatic ring structure;

(iii) $R_{32}$ represents OH, a halogen atom, ONa, OK, or $OR_{42}$; and (iv) $R_{42}$ represents any one of a substituted or unsubstituted alkyl group having 1 to 18 carbon atoms, a substituted or unsubstituted phenyl group, and a substituted or unsubstituted naphthyl group.

<5> According to a fifth aspect of the present invention, there is provided a charge controlling agent, including at least one of compounds each of which has the structure represented by the chemical formula (2) and satisfies the following conditions (1) to (4):

(1) $R_{12}$ and $R_{22}$ independently represent any one of a substituted or unsubstituted alkyl group having 1 to 18 carbon atoms, a substituted or unsubstituted phenyl group, and a substituted or unsubstituted naphthyl group;

(2) at least one of $R_{12}$ and $R_{22}$ contains at least one $SO_2R_{32}$ group as a substituent;

(3) $R_{32}$ represents OH, a halogen atom, ONa, OK, or $OR_{42}$; and (4) $R_{42}$ represents any one of a substituted or unsubstituted alkyl group having 1 to 18 carbon atoms, a substituted or unsubstituted phenyl group, and a substituted or unsubstituted naphthyl group.

<6> According to a sixth aspect of the present invention, there is provided a charge controlling agent, including at least one of compounds each of which has the structure represented by the chemical formula (2) and satisfies at least one of the following conditions (5) and (6):

(5) the chemical formula (2) has a structure represented by the chemical formula (25) and satisfies the following conditions (i) to (iv):

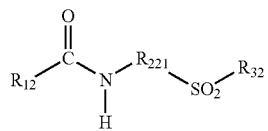

(25)

(i) $R_{12}$ represents any one of an unsubstituted alkyl groups having 1 to 18 carbon atoms, an unsubstituted phenyl group, and an unsubstituted naphthyl group, any one of an alkyl group having 1 to 18 carbon atoms, a phenyl group, and a naphthyl group, each having as one or more substituents one or more of a halogen atom, an alkyl group having 1 to 20 carbon atoms, an alkoxy group (OR, in which R represents an alkyl group having 1 to 20 carbon atoms, a phenyl group; or a naphthyl group), a hydroxyl group, an amino group, a nitro group, carboxylic acid or a carboxylate (salt with Na or K), an acetamide group, an NHPh group, a $CF_3$ group, a $C_2FS$ group, and a $C_3F_7$ group;

(ii) $R_{221}$ represents a substituted or unsubstituted aliphatic hydrocarbon structure having 1 to 18 carbon atoms, a substituted or unsubstituted phenyl group, and a substituted or unsubstituted naphthyl group;

(iii) $R_{32}$ represents OH, a halogen atom, ONa, OK, or $OR_{42}$; and (iv) $R_{42}$ represents any one of a substituted or unsubstituted aliphatic hydrocarbon structure having 1 to 18 carbon atoms, a substituted or unsubstituted phenyl group, and a substituted or unsubstituted naphthyl group, and (6) the chemical formula (2) has a structure represented by the chemical formula (26) and satisfies the following conditions (i) to (iv):

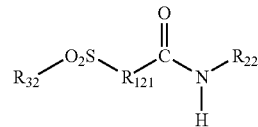

(26)

(i) $R_{121}$ represents any one of a substituted or unsubstituted alkyl group having 1 to 18 carbon atoms, a substituted or unsubstituted phenyl group, and a substituted or unsubstituted naphthyl group;

(ii) $R_{22}$ represents any one of an unsubstituted alkyl group having 1 to 18 carbon atoms, an unsubstituted phenyl group, and an unsubstituted naphthyl group, and any one of an alkyl group having 1 to 18 carbon atoms, a phenyl group, and a naphthyl group, each having as one or more substituents one or more of a halogen atom, an alkyl group having 1 to 20 carbon atoms, an alkoxy group (OR, in which and R represents an alkyl group having 1 to 20 carbon atoms, a phenyl group, or a naphthyl group), a hydroxyl group, an amino group, a nitro group, carboxylic acid or a carboxylate (salt with Na or K), an acetamide group, an NHPh group, a $CF_3$ group, a $C_2F_5$ group, and a $C_3F_7$ group;

(iii) $R_{32}$ represents OH, a halogen atom, ONa, OK, or $OR_{42}$; and (iv) $R_{42}$ represents any one of a substituted or unsubstituted alkyl group having 1 to 18 carbon atoms, a substituted or unsubstituted phenyl group, and a substituted or unsubstituted naphthyl group.

<7> According to a seventh aspect of the present invention, there is provided a charge controlling agent, including at least one of compounds each of which has the structure represented by the chemical formula (2) and satisfies at least one of the following conditions (7) and (8):

(7) the chemical formula (2) has a structure represented by the chemical formula (27) and satisfies the following conditions (i) to (iv):

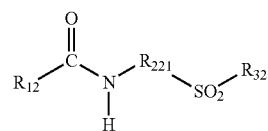

(27)

(i) $R_{12}$ represents any one of a substituted or unsubstituted alkyl group having 1 to 18 carbon atoms, a substituted or unsubstituted phenyl group, and a substituted or unsubstituted naphthyl group;

(ii) $R_{221}$ represents any one of an unsubstituted alkyl group having 1 to 18 carbon atoms, an unsubstituted phenyl group, and an unsubstituted naphthyl group, and any one of an alkyl group having 1 to 18 carbon atoms, a phenyl group, and a naphthyl group each having as one or more substituents one or more of a halogen atom, an alkyl group having 1 to 20 carbon atoms, an alkoxy group (OR, in which R represents an alkyl group having 1 to 20 carbon atoms, a phenyl group, or a naphthyl group), a hydroxyl group, an amino group, a nitro group, carboxylic acid or a carboxylate (salt with Na or K), an acetamide group, an NHPh group, a $CF_3$ group, a $C_2F_5$ group, and a $C_3F_7$ group;

(iii) $R_{32}$ represents OH, a halogen atom, ONa, OK, or $OR_{42}$; and (iv) $R_{42}$ represents any one of a substituted or unsubstituted alkyl group having 1 to 18 carbon atoms, a substituted or unsubstituted phenyl group, and a substituted or unsubstituted naphthyl group, and (8) the chemical formula (2) has a structure represented by the chemical formula (28) and satisfies the following conditions (i) to (iv):

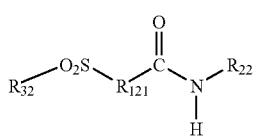

(28)

(i) $R_{121}$ represents any one of an unsubstituted alkyl groups having 1 to 18 carbon atoms, an unsubstituted phenyl group, and an unsubstituted naphthyl group, and any one of an alkyl group having 1 to 18 carbon atoms, a phenyl group, and a naphthyl group each having as one or more substituents one or more of a halogen atom, an alkyl group having 1 to 20 carbon atoms, an alkoxy group (OR, in which R represents an alkyl group having 1 to 20 carbon atoms, a phenyl group, or a naphthyl group), a hydroxyl group, an amino group, a nitro group, carboxylic acid or a carboxylate (salt with Na or K), an acetamide group, an NHPh group, a $CF_3$ group, a $C_2F_5$ group, and a $C_3F_7$ group;

(ii) $R_{22}$ represents a substituted or unsubstituted alkyl group having 1 to 18 carbon atoms, a substituted or unsubstituted phenyl group, and a substituted or unsubstituted naphthyl group;

(iii) $R_{32}$ represents OH, a halogen atom, ONa, OK, or $OR_{42}$; and (iv) $R_{42}$ represents any one of a substituted or unsubstituted alkyl group having 1 to 18 carbon atoms, a substituted or unsubstituted phenyl group, and a substituted or unsubstituted naphthyl group.

<8> According to an eighth aspect of the present invention, there is provided a charge controlling agent, including at least one of compounds each of which has the structure represented by the chemical formula (2) and satisfies the following conditions (1) to (4):

(1) $R_{12}$ and $R_{22}$ independently represent any one of an unsubstituted alkyl group having 1 to 18 carbon atoms, an unsubstituted phenyl group, and an unsubstituted naphthyl group, and any one of an alkyl group having 1 to 18 carbon atoms, a phenyl group, and a naphthyl group each having as one or more substituents one or more of a halogen atom, an alkyl group having 1 to 20 carbon atoms, an alkoxy group (OR, in which R represents an alkyl group having 1 to 20 carbon atoms, a phenyl group, or a naphthyl group), a hydroxyl group, an amino group, a nitro group, carboxylic acid or a carboxylate (salt with Na or K), an acetamide group, an NHPh group, a $CF_3$ group, a $C_2F_5$ group, and a $C_3F_7$ group;

(2) at least one of $R_{12}$ and $R_{22}$ contains at least one $SO_2R_{32}$ group as a substituent;

(3) $R_{32}$ represents OH, a halogen atom, ONa, OK, or $OR_{42}$; and (4) $R_{42}$ represents any one of a substituted or unsubstituted alkyl group having 1 to 18 carbon atoms, a substituted or unsubstituted phenyl group, and a substituted or unsubstituted naphthyl group.

<9> According to a ninth aspect of the present invention, there is provided a toner for developing an electrostatic charge image, characterized by including at least:
  a binder resin;
  a coloring agent; and
  the charge controlling agent according to any one of the first to eighth aspects of the present invention.

<10> According to a tenth aspect of the present invention, there is provided a toner for developing an electrostatic charge image, including:
  a binder resin;
  a coloring agent; and
  a compound represented by the chemical formula (2):

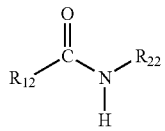

(2)

in which $R_{12}$ and $R_{22}$ satisfy the following conditions (1) to (4);

(1) $R_{12}$ and $R_{22}$ independently represent any one of a substituted or unsubstituted aliphatic hydrocarbon structure, a substituted or unsubstituted aromatic ring structure, and a substituted or unsubstituted heterocyclic structure;

(2) at least one of $R_{12}$ and $R_{22}$ contains at least one $SO_2R_{32}$ group as a substituent;

(3) $R_{32}$ represents OH, a halogen atom, ONa, OK, or $OR_{42}$; and (4) $R_{42}$ represents any one of a substituted or unsubstituted aliphatic hydrocarbon structure, a substituted or unsubstituted aromatic ring structure, and a substituted or unsubstituted heterocyclic structure.

(Further Specific Method of Producing the Compound According to the Present Invention)

Hereinafter, the present invention will be described in more detail with reference to preferable embodiments. The compounds according to the present invention having those respective structures described above show excellent characteristics as charge controlling agents. In addition, a toner for developing an electrostatic charge image containing any one of such charge controlling agents shows excellent advantages when it is used in an image forming apparatus having a development system based on an electrophotographic method. The compound can be produced by, for example, methods as described below.

The compound of the present invention, which contains an amide group and a sulfonic group or a derivative thereof, such as a sulfonic acid ester, a sulfonic acid salt, or a sulfonic acid halide, can be produced by any one of various synthetic methods.

For example, amidation can be performed by a condensation reaction with an amino compound and carboxylic acid compound or a derivative compound thereof.

Hereinafter, for a particularly preferable method of manufacturing the compound of the present invention, a carboxylic acid compound and an amino compound, which can be used for amidation, a process for the amidation, and a process for synthesizing a sulfonic acid ester will be described.

(Carboxylic Acid Compound)

The carboxylic acid compound has a structure represented by the following chemical formula (29):

R—COOH (29)

In the chemical formula (29), R represents a substituted or unsubstituted aliphatic hydrocarbon, a substituted or unsubstituted aromatic hydrocarbon, or a substituted or unsubstituted heterocyclic structure containing at least one of N, S, and O.

Specific examples of the carboxylic acid compound having an aliphatic hydrocarbon skeleton include those described in examples described later.

Specific examples of the carboxylic acid compound having an aromatic ring skeleton include those described in examples described later.

(Amino Compound)

The amino compound has a structure represented by the following chemical formula (30) or (31):

R—NH$_2$ (30)

$\mathrm{R}\diagdown_{\mathrm{NH}}^{}$
$\mathrm{R}\diagup$ (31)

In the chemical formulae (30) and (31), R represents at least one of a substituted or unsubstituted aliphatic hydrocarbon, a substituted or unsubstituted aromatic hydrocarbon, and a substituted or unsubstituted heterocyclic structure containing at least one of N, S, and O. In the chemical formula (31), two Rs may be identical or different.

The amino compound having an aliphatic hydrocarbon skeleton, for example, will be exemplified in examples described later.

The amino compound having an aromatic hydrocarbon skeleton, for example, will be exemplified in examples described later.

(Amidation Reaction)

The condensation reaction of a carboxyl group and an amino group can be performed by any one of methods, such as a method of using a condensation agent and a method of forming a salt and carrying out condensation by a dehydration reaction. Alternatively, a method of converting a carboxyl group into acid chloride and reacting the acid chloride with an amino group can be used.

(Amidation Reaction Using Condensation Agent)

As the manufacturing method of the present invention, a method using a condensation agent will be described in detail.

Examples of the condensation agents, which can be used in the present invention, include phosphate- and carbodiimide-based condensation agents.

A phosphite-based condensation agent is preferably used in the reaction of the present invention.

In the present invention, the reaction may employ any solvent if required.

Examples of the solvent to be used in the present invention include: hydrocarbons, such as hexane, cyclohexane, and heptane; ketones, such as acetone and methyl ethyl ketone; ethers, such as dimethyl ether, diethyl ether, and tetrahydrofuran.

Further, the solvents include halogenated hydrocarbons, such as carbon tetrachloride, dichloroethane, trichloroethane, dichloromethane, and chloroform; aromatic hydrocarbons, such as benzene and toluene; aprotic polar solvents, such as N,N-dimethyl formamide and dimethyl sulfoxide; pyridine derivatives; and the like. Pyridine is particularly preferably used. The amount of the solvent to be used can be appropriately determined in accordance with kinds of a starting material and a base, reaction conditions, and the like.

In this method, a reaction temperature is not particularly limited, but is generally in the range of 0° C. to a boiling point of a solvent. However, it is preferable to perform the reaction at an optimum temperature suited for a condensation agent to be used.

In the method of the present invention, a reaction time is, for example, in the range of 1 to 48 hours.

Here, the purification of a product will be described. The product can be recovered from a reaction solution by distillation, which is a common procedure. For removing contaminants from the product, the product may be subjected to column chromatography with silica gel or alumina, recrystallization or reprecipitation in a solvent in which the product is hardly soluble, extraction procedures by means of liquid separation, or the like, thereby allowing the product to be purified.

(Amidation Reaction Using Acid Chloride)

As the manufacturing method of the present invention, a method of converting a carboxyl group into acid chloride and reacting the acid chloride with an amino group will be described in detail.

The conversion of a carboxyl group into acid chloride may be carried out by a common procedure using thionyl chloride.

The amount of thionyl chloride to be used is in the range of 0.1 to 50.0-fold mole, preferably 1.0 to 20.0-fold mole with respect to carboxylic acid compound. In addition, thionyl chloride itself may be used as a reaction solvent.

The amount of an amino compound to be fed is in the range of 0.1 to 50.0-fold mole, preferably 1.0 to 20.0 with respect to acid chloride. The reaction of the present invention may employ any solvent if required.

Examples of the solvent to be used in the present invention include: hydrocarbons, such as hexane, cyclohexane, and heptane; ketones, such as acetone and methyl ethyl ketone; ethers, such as dimethyl ether, diethyl ether, and tetrahydrofuran.

Further, the solvents include halogenated hydrocarbons, such as carbon tetrachloride, dichloroethane, trichloroethane, dichloromethane, and chloroform; aromatic hydrocarbons, such as benzene and toluene; aprotic polar solvents, such as N,N-dimethyl formamide and dimethyl sulfoxide; pyridine derivatives; and water. The solvent is preferably one in which acid chloride of a carboxylic acid compound as a starting material, an amino compound, and a product can be dissolved. The amount of the solvent to be used can be appropriately determined in accordance with kinds of a starting material and a base, reaction conditions, and the like.

In this method, a reaction temperature is not particularly limited, but is generally in the range of −30° C. to a boiling point of a solvent. However, it is preferable to perform the reaction at an optimum temperature suited for acid chloride of a carboxylic acid compound as a starting material, an amino compound, or a reaction solvent.

In the method of the present invention, a reaction time is, for example, in the range of 1 to 48 hours.

Here, the purification of a product will be described. The product can be recovered from a reaction solution by distillation, which is a common procedure. For removing contaminants from the product, the product may be subjected to column chromatography with silica gel or alumina, recrystallization or reprecipitation in a solvent in which the product is hardly soluble, extraction procedures by means of liquid separation, or the like, thereby allowing the product to be purified.

(Synthetic Reaction of Sulfonic Acid Ester)

A compound containing a sulfonic acid ester is synthesized by using as a starting material a sulfonic acid, a sulfonic acid salt, or a sulfonic acid halide. It can be realized by using an esterifying agent such as trimethylsilyldiazomethane, trimethyl orthoformate, or triethyl orthoformate.

This reaction may use any solvent if required.

Examples of the solvent to be used in the present invention include: hydrocarbons, such as hexane, cyclohexane, and heptane; alcohols, such as methanol and ethanol; ethers, such as dimethyl ether, diethyl ether, tetrahydrofuran, and dioxane.

Further, the solvents include halogenated hydrocarbons, such as carbon tetrachloride, dichloroethane, trichloroethane dichloromethane and chloroform; aromatic hydrocarbons, such as benzene and toluene; aprotic polar solvents, such as N,N-dimethyl formamide and dimethyl sulfoxide; and pyridine derivatives. Chloroform and methanol are particularly preferably used. The amount of the solvent to be used can be appropriately determined in accordance with kinds of a starting material, reaction conditions, and the like.

The amount of the esterifying agent to be used is in the range of 0.1 to 50.0-fold mole, preferably 1.0 to 20.0-fold mole with respect to that of sulfonic acid, a sulfonic acid salt, or a sulfonic acid halide.

In this method, a reaction temperature is not particularly limited, but is generally in the range of −20° C. to 30° C. A reaction time is generally in the range of 1 to 48 hours.

Here, the purification of a product will be described. The product can be recovered from a reaction solution by distillation, which is a common procedure. For removing contaminants from the product, the product may be subjected to column chromatography with silica gel or alumina, recrystallization or reprecipitation in a solvent in which the product is hardly soluble, extraction procedures by means of liquid separation, or the like, thereby allowing the product to be purified.

(Application to Toner)

Applications of the charge controlling agent according to the present invention include applications to toner for developing an electrostatic charge image and an image forming process using the same.

To be specific, the charge controlling agent according to the present invention can be used as a charge controlling agent to be internally or externally added to toner. That is, the present invention relates to a charge controlling agent containing the compound described above and a toner for developing an electrostatic charge image containing the charge controlling agent.

The toner for developing an electrostatic charge image is used for an image forming method or an image forming apparatus described below.

Here, a technology related to toner will be described.

A large number of electrophotographic methods using toner have been known. A general method thereof involves: utilizing a photoconductive substance to form an electrical latent image on an image-bearing member (photosensitive member) by using various means; developing the latent image with toner to form a visible image; transferring the toner image onto an image-receiving material such as paper as required; and fixing the toner image onto the image-receiving material under heating and/or pressure or the like to provide a copy.

Cascade development, magnetic brush development, impression development, or the like has been known as a method of visualizing an electrical latent image. A method involving: using magnetic toner and a rotation developing sleeve having a magnetic pole at its center; and allowing the magnetic toner to flow from a place on the developing sleeve to a place on a photosensitive member in a magnetic field has also been used. Development methods to be used for developing an electrostatic latent image are classified into: a two-component development method involving the use of a two-component developer composed of toner and a carrier; and a one-component development method involving the use of a one-component developer composed only of toner and using no carrier. Here, a colored fine particle generally referred to as toner contains a binder resin and a coloring agent as essential ingredients, and further contains a charge controlling agent, magnetic powder, or the like as required. The compound according to the present invention can be used for such toner.

For example, the compound represented by the chemical formula (2) is used as a charge controlling agent to be used in the composition of toner for developing an electrostatic charge image, whereby excellent charging property can be provided and good dispersibility of the compound into a toner resin and good spent property can be provided.

In addition, when the charge controlling agent according to the present invention is used, toner for developing an electrostatic charge image can be provided, which has suppressed occurrence of image fogging at the time of output by an image forming apparatus and excellent transferability.

Further, a charge controlling agent using the compound according to the present invention can be colorless or have weakened tint. Therefore, an arbitrary coloring agent can be selected in accordance with a hue required for color toner irrespective of the charge controlling agent. A charge controlling agent which is colorless or has weak tinting is preferable because such the charge controlling agent hardly inhibits the original hue of a dye or a pigment.

Toner containing the charge controlling agent of the present invention has a high specific charge amount and good stability with time. Therefore, a vivid image can be stably obtained in electrostatic image formation even if the toner is stored for a long period of time.

In addition, the toner is colorless or has extremely weak tint, and has good negative chargeability. Therefore, each of black negatively charged toner and color toner can be produced.

Here, a charge controlling agent will be described in further detail. The use of the charging property of a binder resin itself without the use of a charge controlling agent may be adopted as a method of imparting charge to toner. In this case, however, stability of charging with time and humidity resistance become poor, and good image quality is not obtained in some cases. Therefore, a charge controlling agent is generally added for maintaining and controlling the charge of toner. Examples of a charge controlling agent conventionally known in the art include: charge controlling agents each having negative frictional chargeability such as azo dye metal complexes, metal complexes of aromatic dicarboxylic acids, and metal complexes of salicylic acid derivatives; and positive charge controlling agents such as nigrosin-based dyes, triphenylmethane-based dyes, and organic tin compounds including various quaternary ammonium salt dibutyltin oxides. When the compound according to the present invention is used for a charge controlling agent, the compound may be used in combination with any one of the above-mentioned conventionally known charge controlling agents.

(Addition of Compound According to the Present Invention to Toner)

In the present invention, a method involving internal addition to toner or a method involving external addition to toner may be used as a method of incorporating a charge controlling agent composed of any one of the compounds described above into toner. The addition amount of a charge controlling agent in the case of internal addition is generally in the range of 0.1 to 50 mass %, or preferably 0.2 to 20 mass % with respect to the total mass of a toner binder and the charge controlling agent. An addition amount of less than 0.1 mass % is not preferable because the degree of improvement in chargeability of toner may not be remarkable. On the other hand, an addition amount in excess of 50 mass % may not be preferable from the viewpoint of economy. A mass ratio between a toner binder and a charge controlling agent in the case of external addition is preferably in the range of (0.01 to 5 mass % with respect to the total mass of the toner binder and the charge controlling agent.

The composition of the toner for developing an electrostatic charge image of the present invention is generally 0.1 to 50 mass % of a charge controlling agent, 20 to 95 mass % of a toner binder, and 0 to 15 mass % of a coloring material based on the toner mass.

The toner may contain 60 mass % or less of magnetic powder (for example, powder of a ferromagnetic metal such as iron, cobalt, or nickel, or a compound such as magnetite, hematite, or ferrite) serving also as a coloring material as required. The toner may further contain various additives (such as a lubricant (for example, polytetrafluoroethylene, low-molecular-weight polyolefin, an aliphatic acid, or a metal salt or amide thereof) and other charge controlling agents (for example, a metal-containing azo dye and a salicylic acid metal salt)). Hydrophobic colloidal silica fine powder or the like may also be used for improving the fluidity of the toner. A total amount of those additives is generally 10 mass % or less based on the toner mass.

In the toner of the present invention, in one toner particle, at least part of a toner binder preferably forms a continuous phase containing no charge controlling agent and at least part of a charge controlling agent preferably forms a discontinuous domain containing no toner binder. As compared to the case where a charge controlling agent is completely compatible with a toner binder without the formation of a discontinuous domain, the added charge controlling agent is easily exposed to the toner surface, and a small addition amount can exert an effect. The domain has a dispersed particle size in the range of preferably 0.01 to 4 μm, or more preferably 0.05 to 2 μm. A dispersed particle size in excess of 4 μm provides insufficient dispersibility, so there arises a problem in that a charge amount distribution becomes wide and transparency of toner deteriorates. In addition, a dispersed particle size of less than 0.01 μm requires a large addition amount of a charge controlling agent as in the case where a charge controlling agent is completely compatible with a toner binder without the formation of a discontinuous domain. The fact that at least part of the charge controlling agent forms a discontinuous domain and the dispersed particle size of the domain can be confirmed by observing a section of toner by means of a transmission electron microscope or the like. For clearly observing an interface, a toner section may be observed by means of an electron microscope after the section has been stained with ruthenium tetroxide, osmium tetroxide, or the like.

<Other Components>

Hereinafter, other components constituting the toner for developing an electrostatic charge image of the present invention will be described. The toner for developing an electrostatic charge image according to the present invention may contain a binder resin, a coloring agent, and other additives to be added as required as well as the above-mentioned charge controlling agent.

(Binder Resin)

First, a thermoplastic resin which is generally used for toner can be used as the binder resin.

Examples of an available thermoplastic resin include polystyrene, polyacrylate, a styrene-acrylate copolymer, polyvinyl chloride, polyvinyl acetate, polyvinylidene chloride, a phenol resin, an epoxy resin, and a polyester resin.

Any one of the binder resins that are generally used for producing toner can be used, and the binder resin to be used is not particularly limited.

In addition, the charge controlling agent of the present invention can be mixed with a binder resin before production of toner, and the mixture can be used as a composition for forming binder including a charge controlling ability.

Examples of the binder resin include a styrene-based polymer, a polyester-based polymer, an epoxy-based polymer, a polyolefin-based polymer, and a polyurethane-based polymer. Each of them may be used alone, or two or more of them may be used in combination.

Examples of the styrene-based polymer include: a copolymer of styrene and (meth)acrylate and copolymers of other monomers copolymerizable with them; a copolymer of styrene and a diene-based monomer (such as butadiene or isoprene); and copolymers of other monomers copolymerizable with them.

An example of the polyester-based polymer includes a polycondensate of an aromatic dicarboxylic acid and an alkylene oxide adduct of an aromatic diol. Examples of the epoxy-based polymer include a product of a reaction between an aromatic diol and epichlorohydrin and a denatured product thereof. Examples of the polyolefin-based polymer include copolymer chains of polyethylene, polypropylene, and other monomers copolymerizable with them. An example of the polyurethane-based polymer includes a polyadductt of an aromatic diisocyanate and an alkylene oxide adduct of an aromatic diol.

Specific examples of the binder resin to be used in combination with the charge controlling agent of the present invention include: a polymer of any one of the polymerizable monomers described below; and a mixture of the polymerizable monomers or a product of copolymerization.

Specific examples thereof which may preferably be used include a styrene-based polymer such as a styrene/acrylic acid copolymer or a styrene/methacrylic acid-based copolymer, a polyester-based polymer, an epoxy-based polymer, a polyolefin-based polymer, and a polyurethane-based polymer.

(Cross-Linking Agent)

In forming a binder resin to be used in combination with the charge controlling agent of the present invention, a cross-linking agent may be used. An example of a divalent cross-linking agent includes divinyl benzene.

(Polymerization Initiator)

In addition, in forming a binder resin to be used in combination with the charge controlling agent of the present invention, a polymerization initiator such as 2,2'-azobis(4-methoxy-2,4-dimethylvaleronitrile) may be used as required. The polymerization initiator is used at a concentration of 0.05 part by mass or more (preferably 0.1 to 15 parts by mass) with respect to 100 parts by mass of the monomer.

to be internally added is less than 0.1 mass %, a charge

<Charge Controlling Agent: other than Compound of the Present Invention>

A conventionally used charge controlling agent other than the charge controlling agent of the present invention may be used in combination with the charge controlling agent of the present invention. Specific examples thereof include a nigrosin-based dye, a quaternary ammonium salt, and a monoazo-based metal complex salt dye.

The addition amount of the charge controlling agent can be determined in consideration of conditions such as chargeability of a binder resin, a production method including the addition amount and a dispersion method of a coloring agent, and chargeability of any one of the other additives.

For example, the charge controlling agent may be used in the ratio of 0.1 to 20 parts by mass, or preferably 0.5 to 10 parts by mass with respect to 100 parts by mass of the binder resin In addition to the above, an inorganic particle of a metal oxide or the like, or an inorganic substance the surface of which is treated with any one of the above-mentioned organic substances may be used. Any one of those charge controlling agents may be used while being mixed with and added to a binder resin, or may be used while being allowed to adhere to a toner particle surface.

<Coloring Agent>

Any one of the coloring agents that are generally used for producing toner can be used as a coloring agent constituting the toner for developing an electrostatic charge image of the present invention without particular limitation. Examples of an available coloring agent include carbon black, titanium white, a monoazo-based red pigment, a disazo-based yellow pigment, a quinacridone-based magenta pigment, an anthraquinone dye, and any other kinds of pigments and/or dyes.

In addition, when the toner for developing an electrostatic charge image of the present invention is used as two-component full-color toner, any one of such coloring agents as described below may be used. For example, carbon black, C.I. Pigment Blue 15, Hanzayellow G, or C.I. Pigment Red 114 can be used.

In the present invention, each of the above-mentioned pigments may be used alone, but it is preferable to use a dye and a pigment in combination to improve the visibility in terms of image quality of a full-color image.

Each of the dyes and pigments may be used alone, or two or more of them may be arbitrarily mixed for obtaining a desired toner hue.

The content of any one of such coloring agents as described above in toner may be widely changed in accordance with a desired coloring effect and the like.

For obtaining best toner properties, that is, in consideration of coloring power of a printed letter, form stability of toner, scattering of toner, and the like, any one of those coloring agents is generally used in an amount as follows: about 0.1 to 60 parts by mass, or preferably about 0.5 to 20 parts by mass with respect to 100 parts by mass of a binder resin.

<Other Components of Toner>

The toner for developing an electrostatic charge image of the present invention may contain any one of the following compounds as well as the binder resin and coloring agent components described above to such an extent that an effect of the present invention is not adversely affected. For example, waxes such as silicone resin, polyester, polyurethane and polyamide are included.

Of those, examples of a wax preferably used include low-molecular-weight polypropylene and a by-product thereof, low-molecular-weight polyester and an ester-based wax, and an aliphatic derivative. Waxes obtained by differentiating those waxes depending on a molecular weight by using any one of various methods are also preferably used in the present invention. Oxidation, block copolymerization, or graft denaturation may also be performed after the differentiation.

The toner for developing an electrostatic charge image of the present invention becomes preferable toner when the toner contains such wax components as described above and these wax components are dispersed into the binder resin in a substantially spherical and/or spindle island fashion in the case where a toner section is observed by means of a transmission electron microscope (TEM).

<Method of Producing Toner>

Any one of the conventionally known methods can be used as a specific method of producing the toner for developing an electrostatic charge image of the present invention having such a structure as described above. The toner for developing an electrostatic charge image of the present invention can be produced by means of, for example, a so-called pulverization method of obtaining toner by using the following steps. That is, to be specific, resins such as a binder resin, a charge controlling agent of the present invention, and other charge controlling agent and a wax to be added as required are sufficiently mixed in a mixer such as a Henschel mixer or a ball mill.

The resultant mixture is melted and kneaded by using a heat kneader such as a heat roll, a kneader, or an extruder to make the resins compatible with each other, and into the kneaded product, a pigment or a dye as a coloring agent, or a magnetic substance, and an additive such as a metal compound to be added as required are dispersed or dissolved.

After the resultant is cooled for solidification, the solidified product is pulverized by means of a pulverizer such as a jet mill or a ball mill, and the pulverized product is classified, to thereby obtain the toner for developing an electrostatic charge image of the present invention having a desired particle size. A multi-division classifier is preferably used in the classification step in terms of production efficiency.

The toner for developing an electrostatic charge image of the present invention having a desired particle size can also be obtained by: mixing a binder resin and a charge controlling agent and the like in a solution by using a solvent; subjecting the solution to stirring treatment; placing the resultant in water for reprecipitation; filtering and drying the precipitate; pulverizing the solidified product by means of a pulverizer such as a jet mill or a ball mill; and classifying the pulverized product. A multi-division classifier is preferably used in the classification step in terms of production efficiency. Examples of the solvent include an aromatic hydrocarbon such as toluene or xylene, a halogenated compound such as chloroform or ethylene dichloride, a ketone such as acetone or methyl ethyl ketone, and an amide such as dimethylformamide.

The toner for developing an electrostatic charge image of the present invention can also be produced by means of a so-called polymerization method described below. That is, in this case, the toner for developing an electrostatic charge image of the present invention can be obtained by: mixing and dispersing a polymerizable monomer of a binder resin, a charge controlling agent, a pigment or a dye as a coloring agent, or a magnetic substance, and, as required, materials such as a cross-linking agent, a polymerization initiator, a wax, another binder resin, and other additives; subjecting the resultant mixture to suspension polymerization in an aqueous dispersion medium in the presence of a surfactant or the like to synthesize polymerizable colored resin particles; subjecting the resultant particles to solid-liquid separation; drying the resultant product; and classifying the resultant product as required. Further, a colored fine particle containing no charge controlling agent may be prepared according to the above-mentioned method, and the above-mentioned polymer may be fixed and added to particle surface by means of a mechanochemical method or the like alone or together with an external additive such as colloidal silica.

(Silica External Additive)

In the present invention, silica fine powder is preferably externally added to toner produced by means of such a method as described above for improving charging stability, developability, fluidity, and durability. One having a specific surface area by nitrogen adsorption measured by means of a BET method of 20 $m^2/g$ or more (particularly 30 to 400 $m^2/g$) is used at this time as the silica fine powder to provide good results. The amount of the silica fine powder to be used in this case is about 0.01 to 8 parts by mass, or preferably about 0.1 to 5 parts by mass with respect to 100 parts by mass of toner particles.

The silica fine powder to be used at this time can preferably be treated as required with any one of the treatments described below.

Examples of the treatments include substances such as silicone varnish, various denatured silicone varnishes, silicone oil, various denatured silicone oils, silane coupling agents, silane coupling agents each having a functional group, and other organic silicon compounds.

Those treatments may be mixed before use.

(Inorganic Powder)

Any one of the inorganic powders described below is also preferably added for improving the developability and durability of the toner.

Examples of the inorganic fine powders include: oxides of metals such as magnesium, zinc, aluminum, cerium, cobalt, iron, zirconium, chromium, manganese, strontium, tin, and antimony; composite metal oxides such as calcium titanate, magnesium titanate, and strontium titanate; metal salts such as calcium carbonate, magnesium carbonate, and aluminum carbonate; clay minerals such as kaolin; phosphoric acid compounds such as apatite; silicon compounds such as silicon carbide and silicon nitride; and carbon powders such as carbon black and graphite. Of those, fine powder of zinc oxide, aluminum oxide, cobalt oxide, manganese dioxide, strontium titanate, or magnesium titanate is preferably used.

(Lubricant)

Any one of the lubricant powders described below may be further added to the toner. Examples of the lubricant powders include: fluorine resins such as Teflon and polyvinylidene fluoride; fluorine compounds such as carbon fluoride; aliphatic metal salts such as zinc stearate; aliphatic acid derivatives such as an aliphatic acid and an aliphatic ester; and molybdenum sulfide.

<With Regard to Carrier>

The toner for developing an electrostatic charge image of the present invention can be applied to any one of the conventionally known various toners. For example, the toner for developing an electrostatic charge image can be singly used as a nonmagnetic one-component developer. Alternatively, the toner for developing an electrostatic charge image of the present invention can be used as a nonmagnetic toner constituting a magnetic two-component developer together with a magnetic carrier, a magnetic toner to be singly used as a magnetic one-component toner, or the like. Any one of conventionally known carriers can be used as a carrier to be used for a two-component development method. To be specific, particles having an average particle size of 20 to 300 µm and formed of metals such as surface-oxidized or unoxidized iron, nickel, cobalt, manganese, chromium, and a rare earth, and alloys or oxides of them can be used as carrier particles. In the carrier to be used in the present invention, the surfaces of the carrier particles are preferably attached or coated with substances such as a styrene-based resin, an acrylic resin, a silicone-based resin, a fluorine-based resin, and a polyester resin.

<Magnetic Toner>

The toner for developing an electrostatic charge image of the present invention may contain a magnetic material in its toner particles to serve as magnetic toner. In this case, the magnetic material can also function as a coloring agent.

Examples of the magnetic material to be used at this time include: iron oxides such as magnetite, hematite, and ferrite; and metals such as iron, cobalt, and nickel, and alloys and mixtures of these metals with metals such as aluminum, cobalt, copper, lead, magnesium, tin, zinc, antimony, beryllium, bismuth, cadmium, calcium, manganese, selenium, titanium, tungsten, and vanadium. The magnetic material that can be used in the present invention has an average particle size of preferably 2 µm or less, or more preferably about 0.1 to 0.5 µm. The amount of the magnetic material in the toner is preferably 20 to 200 parts by mass, or particularly preferably 40 to 150 parts by mass with respect to 100 parts by mass of the binder resin.

It is necessary to make it possible to faithfully develop a finer latent image dot for achieving additionally improved image quality. Therefore, the weight average particle size of the toner particles for developing an electrostatic charge image of the present invention is preferably adjusted to fall within the range of 4 µm to 9 µm. That is, toner particles having a weight average particle size of less than 4 µm are not preferable because transfer efficiency reduces and a large amount of transfer residual toner is apt to remain on a photosensitive member, which tends to be responsible for image unevenness based on fogging and insufficient transfer. Toner particles having a weight average particle size in excess of 9 µm are apt to cause scattering of a letter or a line image.

In the present invention, the average particle size and particle size distribution of the toner were measured by using an apparatus such as a Coulter Counter TA-II or a Coulter Multisizer (each manufactured by Beckman Coulter Inc.).

The apparatus is connected with an interface (manufactured by Nikkaki-Bios) and a personal computer for outputting a number distribution and a volume distribution. A 1% aqueous solution of NaCl is prepared as an electrolyte to be used at this time by using extra-pure sodium chloride. For example, a commercially available ISOTON R-II (manufactured by Coulter Scientific Japan Ltd.) can also be used as an electrolyte. A specific measurement method is as follows. 100 to 150 ml of the electrolyte are added with 0.1 to 5 ml of a surfactant (preferably an alkylbenzene sulfonate) as a dispersant. Further, 2 to 20 mg of a sample to be measured are added to prepare a sample for measurement. At the time of measurement, the electrolyte into which the sample to be measured was suspended was subjected to dispersion treatment for about 1 to 3 min by using an ultrasonic dispersing unit.

After that, the volume and number of toner having a particle size of 2 µm or more were measured by means of a 100 µm aperture as an aperture using the Coulter counter TA-II to calculate a volume distribution and a number distribution. Subsequently, a weight average particle size (D4) on a volume basis and a length average particle size (D1) on a number basis were determined from the volume distribution according to the present invention and the number distribution according to the present invention, respectively.

<Charge Amount>

The toner for developing an electrostatic charge image of the present invention has a charge amount per unit mass (two-component method) of preferably −10 to −80 µC/g, or more preferably −15 to 70 µC/g for improving transfer efficiency in a transfer method involving the use of a transfer member to which a voltage is applied.

Figure 5:
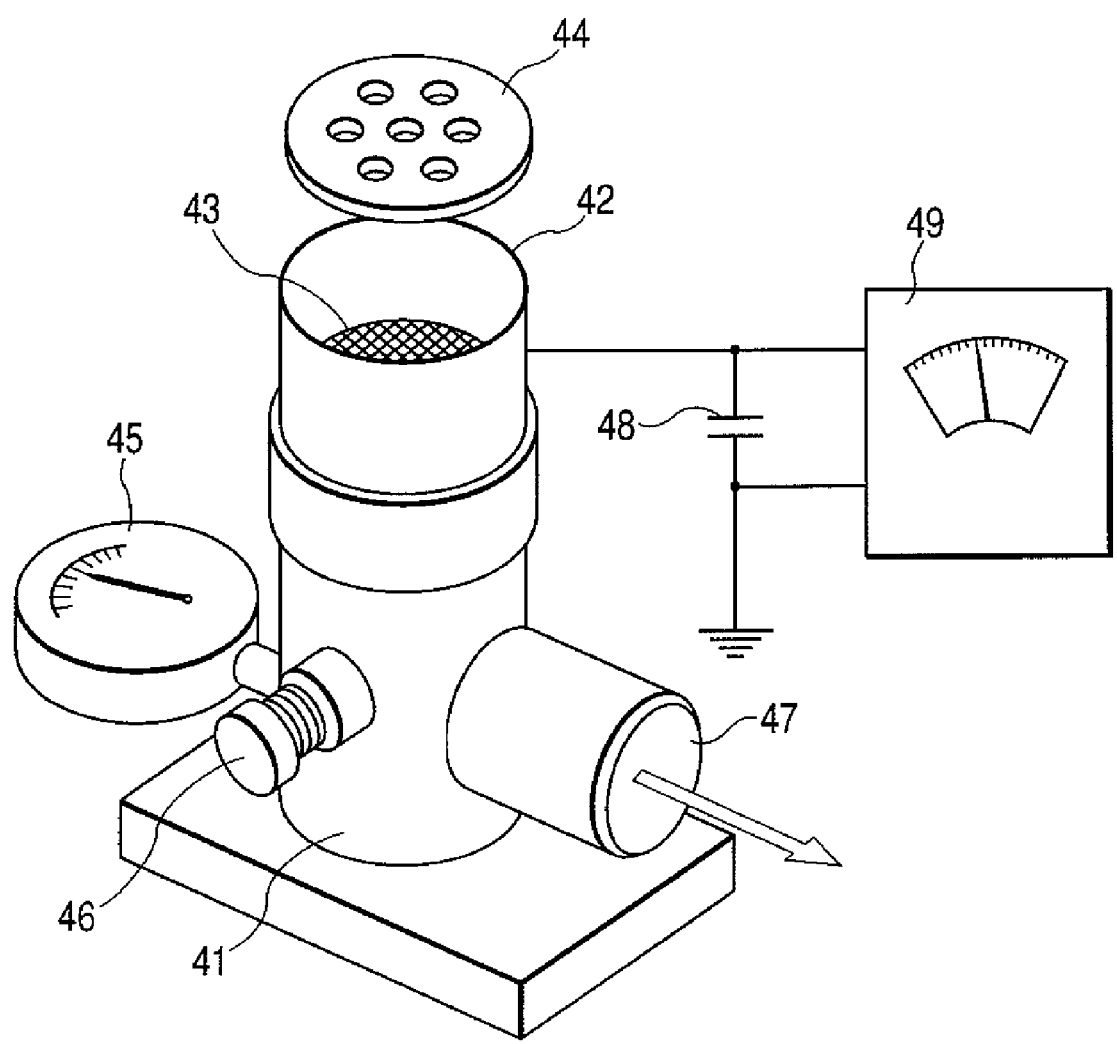
FIG. 5 is a schematic diagram illustrating a blow-off charge amount measuring device for measuring the charge amount of the toner.

A method of measuring a charge amount according to a two-component method used in the present invention will be described below. A charge amount measuring device shown in FIG. 5 was used for the measurement. First, an EFV 200/300 (manufactured by Powder Tech) is used as a carrier, and a mixture obtained by adding 0.5 g of toner to be measured to 9.5 g of the carrier is placed in a polyethylene bottle having a volume of 50 to 100 ml. The bottle is set in a shaker with a constant amplitude, and is shaken for a predetermined period of time under shaking conditions of: an amplitude of 100 mm; and a shaking speed of 100 reciprocations/min. Next, 1.0 to 1.2 g of the mixture are placed in a metallic measurement container 42, which has a 500 mesh screen 43 at its bottom, of a charge amount measuring device 41 shown in FIG. 5, and the container is capped with a metallic cap 44. The mass of the entire measurement container 42 at this time is measured and designated by W1 (g). Next, the toner in the container is sucked through a suction port 47 by means of a sucker (not shown) (at least part of the sucker in contact with the measurement container 42 is made of an insulator), and an air quantity regulating valve 46 is adjusted in such a manner that a vacuum gage 45 indicates a pressure of 2,450 Pa (250 mmAq). Suction is performed for 1 min in this state to suck and remove the toner. The potential of a potentiometer 49 at this time is designated by V (volt). Here, reference numeral 48 denotes a capacitor having a capacity of C (μF). In addition, the mass of the entire measuring device after the suction is measured and designated by W2 (g). The frictional charge amount of the toner is calculated from those measured values according to the following equation.

Frictional charge amount (μC/g)=C×V/(W1−W2)     Equation:

Those operations are performed in a predetermined environment (e.g., predetermined temperature and humidity conditions).

<Method of Measuring Molecular Weight of Hinder Resin and Molecular Weight Distribution of the Resin>

In addition, a binder resin to be used as a constituent of the toner for developing an electrostatic charge image of the present invention preferably has a peak in a low-molecular-weight region in the range of 3,000 to 15,000 in a molecular weight distribution by means of GPC particularly when produced by means of the pulverization method. That is, when a GPC peak in a low-molecular-weight region exceeds 15,000, an improvement in transfer efficiency may be hardly sufficient. It is not preferable to use a binder resin having a GPC peak in a low-molecular-weight region of less than 3,000 because fusion is apt to occur at the time of surface treatment.

In the present invention, the molecular weight of the binder resin was measured by means of gel permeation chromatography (GPC). A specific measurement method according to GPC involved: using for measurement a sample obtained by extracting toner with a tetrahydrofuran (THF) solvent for 20 hours by using a Soxhlet extractor; connecting A-801, 802, 803, 804, 805, 806, and 807 manufactured by Showa Denko K. K. to constitute a column; and measuring a molecular weight distribution using a calibration curve of a standard polystyrene resin. In addition, in the present invention, a binder resin having a ratio (Mw/Mn) between a weight average molecular weight (Mw) and a number average molecular weight (Mn) measured as described above in the range of 2 to 100 is preferably used.

<Glass Transition Point of Toner>

Further, the toner of the present invention is prepared by using an appropriate material to have a glass transition point Tg in the range of preferably 40° C. to 75° C., or more preferably 52° C. to 70° C. from the viewpoints of fixability and storage stability. In this case, the glass transition point Tg may be measured by using a differential scanning calorimeter of a high-precision inner heat input compensation type such as a DSC-7 manufactured by PerkinElmer, Inc. A measurement method is performed in accordance with ASTM D 3418-82. In the present invention, it is recommended that, in measuring the glass transition point Tg, a DSC curve be used, which is measured by: increasing the temperature of a sample to be measured once to take entire hysteresis; quenching the sample; and increasing the temperature again at a rate of temperature increase of 10° C./min in the temperature range of 0 to 200° C.

The inventors of the present invention have found that the charge controlling agent described above exhibits extremely excellent properties. This will be shown in Examples described later.

EXAMPLES

First, a compound and a method of producing the same provided by the present invention will be described by way of Examples A-1 to O-1, A-2 to L-2, B-3, B-4, and H-3. Next, usefulness of a charge controlling agent according to the present invention will be described by way of Examples 1 to 40 while using comparative examples.

The charge controlling agent and toner for developing an electrostatic charge image using the same according to the present invention are not limited to the following examples.

In each of the following experiments, the structure of the resultant compound was determined through analysis according to nuclear magnetic resonance ($^1$H-NMR) spectrum and Fourier transformation-infrared absorption (FT-IR) spectrum. Apparatus used here were as follows: $^1$H-NMR (FT-NMR: Bruker DPX 400 (trade name); resonance frequency: 400 MHz; measured nuclear species: 1H; solvent used: heavy DMSO or heavy chloroform; measurement temperature: room temperature); and FT-IR (Nicolet AVATAR 360FT-IR (trade name)).

Example A-1

Under a nitrogen atmosphere, 1.0 g (8.2 mmol) of benzoic acid and 2.1 g (12.3 mmol) of 2-aminobenzene sulfonic acid were placed in a 100-ml three-necked flask and then added with 30 ml of pyridine, followed by being stirred. Subsequently, 3.2 ml (12.3 mmol) of triphenyl phosphite was added to the mixture, followed by heating at 115° C. for 6 hours. After completion of the reaction, the solvent was distilled off and 30 ml of chloroform was then added to dissolve a product. The resultant product was washed five times with 30 ml in total of 4N hydrochloric acid and chloroform was then distilled off to collect the product. The resultant product was dissolved in 5 ml of chloroform and then purified by column chromatography filled with silica gel. The product thus collected was dried under reduced pressure, thereby obtaining 1.0 g of the product (3.6 mmol, 44% in yield). From the results of $^1$H-NMR, an additional signal derived from an amide group was observed. In addition, a signal derived from a benzene ring proton of the benzoic acid was shifted. Consequently, the resultant product was confirmed as a compound represented by the chemical formula (A-1) described below.

In addition, the preparation method was scaled up to produce 50 g of the compound. The compound was provided as Exemplified Compound A-1 in Examples 1 to 40.

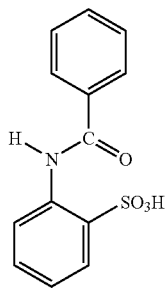

(A-1)

Examples B-1 to O-1

Experiments were carried out in the same manner as in Example A-1 using carboxylic acid compounds, amino compounds, triphenyl phosphite, and 30 ml of pyridine, respectively. The mixing ratios (unit: g, ml, or mmol) of those agents and structures of compounds obtained were listed in Tables A-1 to A-3, respectively.

An amino compound used for the synthesis of Compound N-1 was synthesized by the method described in Journal of Organic Chemistry, 1985, 50, 3336-3341 and then used in the experiment. An amino compound used for the synthesis of Compound O-1 was prepared by the method described in Journal of the American Chemical Society, 1962, 84, 3289-3295, where it was converted into 2-pentanol and reacted with ethanol, and then used in the experiment.

Figure 2:
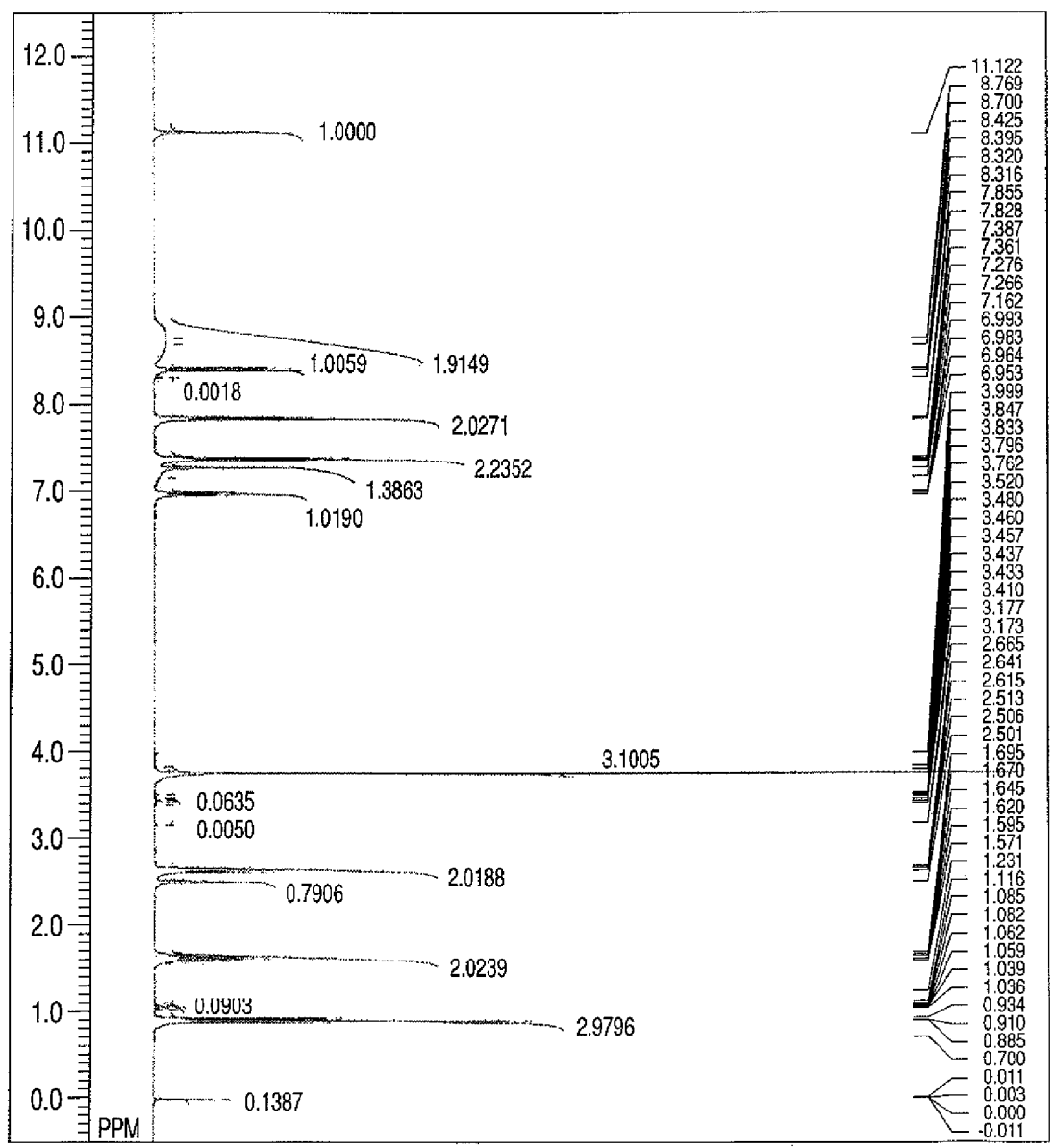
FIG. 2 illustrates the results of $^1$H-NMR measurement of the exemplified compound E-1.

The resultant product was confirmed by a $^1$H-NMR measurement by confirming a signal derived from the amide group. The results of the $^1$H-NMR measurement of B-1 are shown in FIG. 1. In addition, the results of the $^1$H-NMR measurement of E-1 are shown in FIG. 2.

Further, the preparation method was scaled up to produce 50 g of each of the compounds. Those compounds were provided as Exemplified Compounds B-1 to O-1 in Examples 1 to 40.

Compound 1 will be explained in below using the following table. In table, the symbols such as A-1, B-1, etc. At right lower side of chemical formulas show the compounds obtained in Example A-1, Example B-1, etc.

TABLE A-1

| | | Carboxylic acid compound | | | Amino compound | | | Triphenyl phosphite | |
|---|---|---|---|---|---|---|---|---|---|
| Compound 1 | | Name | Amount added (g) | Amount added (mmol) | Name | Amount added (g) | Amount added (mmol) | Amount added (ml) | Amount added (mmol) |
| A | (A-1) | Benzoic acid | 1.00 | 8.19 | 2-aminobenzene-sulfonic acid | 2.13 | 12.29 | 3.2 | 12.3 |

TABLE A-2

| | | Carboxylic acid compound | | | Amino compound | | | Triphenyl phosphite | |
|---|---|---|---|---|---|---|---|---|---|
| Compound 1 | | Name | Amount added (g) | Amount added (mmol) | Name | Amount added (g) | Amount added (mmol) | Amount added (ml) | Amount added (mmol) |
| B | B-1 | 4-propyl benzoic acid | 1.00 | 6.09 | 2-aminobenzene sulfonic acid | 1.58 | 9.14 | 2.4 | 9.1 |

TABLE A-2-continued

| Compound 1 | | Carboxylic acid compound | | | Amino compound | | | Triphenyl phosphite | |
|---|---|---|---|---|---|---|---|---|---|
| | | Name | Amount added (g) | Amount added (mmol) | Name | Amount added (g) | Amount added (mmol) | Amount added (ml) | Amount added (mmol) |
| C | C-1 | 4-butyl-2-methyl benzoic acid | 1.00 | 5.20 | 3-aminobenzene sulfonic acid | 1.35 | 7.80 | 2.0 | 7.8 |
| D | D-1 | 3-acetyl benzoic acid | 1.00 | 5.15 | 4-aminobenzene sulfonic acid | 1.34 | 7.72 | 2.0 | 7.7 |
| E | E-1 | 4-propyl benzoic acid | 1.00 | 6.09 | 4-methoxy aniline-2-sulfonic acid | 1.86 | 9.14 | 2.4 | 9.1 |

TABLE A-2-continued

| | Carboxylic acid compound | | | Amino compound | | | Triphenyl phosphite | |
|---|---|---|---|---|---|---|---|---|
| Compound 1 | Name | Amount added (g) | Amount added (mmol) | Name | Amount added (g) | Amount added (mmol) | Amount added (ml) | Amount added (mmol) |
| F 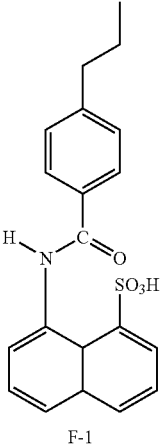 F-1 | 4-propyl benzoic acid | 1.00 | 6.09 | 1-naphthyl amine-8-sulfonic acid | 2.04 | 9.14 | 2.4 | 9.1 |
| G 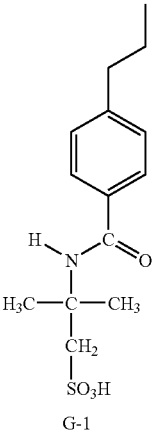 G-1 | 4-propyl benzoic acid | 1.00 | 6.09 | 2-amino-2-methyl propane sulfonic acid | 1.40 | 9.14 | 2.4 | 9.1 |
| H 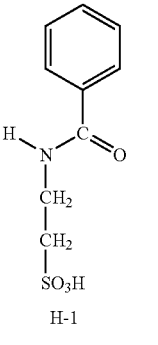 H-1 | Benzoic acid | 1.00 | 8.19 | Taurine (2-aminoethane sulfonic acid) | 1.54 | 12.29 | 3.2 | 12.3 |

TABLE A-3

| Compound 1 | Carboxylic acid compound | | | Amino compound | | | Triphenyl phosphite | |
|---|---|---|---|---|---|---|---|---|
| | Name | Amount added (g) | Amount added (mmol) | Name | Amount added (g) | Amount added (mmol) | Amount added (ml) | Amount added (mmol) |
| I (I-1) | Decanoic acid | 1.00 | 5.81 | 2-aminobenzene sulfonic acid | 1.51 | 8.71 | 2.3 | 8.7 |
| J (J-1) | 3,3,3-trifluoro propionic acid | 1.00 | 7.81 | 2-aminobenene sulfonic acid | 2.03 | 11.71 | 3.1 | 11.7 |
| K (K-1) | 1-naphthalene carboxylic acid | 1.00 | 5.81 | 2-aminobenzene sulfonic acid | 1.51 | 8.71 | 2.3 | 8.7 |
| L (L-1) | 3-(2-naphthalenyloxy sulfonyl benzoic acid) | 1.00 | 3.05 | 2-aminobenzene sulfonic acid | 0.79 | 4.57 | 1.2 | 4.6 |

TABLE A-3-continued

| Compound 1 | | Carboxylic acid compound | | | Amino compound | | | Triphenyl phosphite | |
|---|---|---|---|---|---|---|---|---|---|
| | | Name | Amount added (g) | Amount added (mmol) | Name | Amount added (g) | Amount added (mmol) | Amount added (ml) | Amount added (mmol) |
| M | M-1 | 4-propyl benzoic acid | 1.00 | 6.09 | 4-aminobenzene sulfonic acid phenyl ester | 2.28 | 9.14 | 2.4 | 9.1 |
| N | N-1 | 4-propyl benzoic acid | 1.00 | 6.09 | 4-aminobenene sulfonic acid-4-nitrophenyl ester | 2.69 | 9.14 | 2.4 | 9.1 |
| O | O-1 | 4-propyl benzoic acid | 1.00 | 6.09 | 4-aminobenzene sulfonic acid ethyl ester | 1.84 | 9.14 | 2.4 | 9.1 |

Example A-2

In a 50-ml eggplant flask, 0.30 g (1.1 mmol) of the product (Exemplified Compound A-1) obtained in Example A-1 was added and then dissolved by adding 15 ml of chloroform and 5 ml methanol, followed by cooling to 0° C. The solution was added with 5.4 ml (10.8 mmol) of a 2-mol/l trimethyl silyl-diazomethane-hexane solution (manufactured by Sigma-Aldrich Co.) and then stirred for 3 hours. After completion of the reaction, the solvent was distilled off by an evaporator, followed by collecting the resultant product. Further, 15 ml of chloroform and 5 ml of methanol were added to dissolve the product again. Subsequently, the solvent was distilled off by an evaporator. This operation was repeated 3 times. The collected product was dried under reduced pressure to obtain 0.30 g of the product (1.0 mmol, 95% in yield). A $^1$H-NMR measurement showed a peak derived from methyl sulfonate at 3 to 4 ppm, so that the resultant product was confirmed as a compound represented by the formula (A-2) described below.

In addition, the preparation method was scaled up to produce 50 g of the compound. The compound was provided as Exemplified Compound A-2 in Examples 1 to 40.

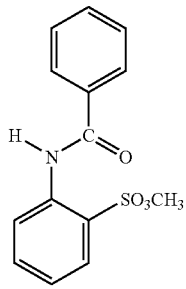

(A-2)

Examples B-2 to L-2

Figure 3:
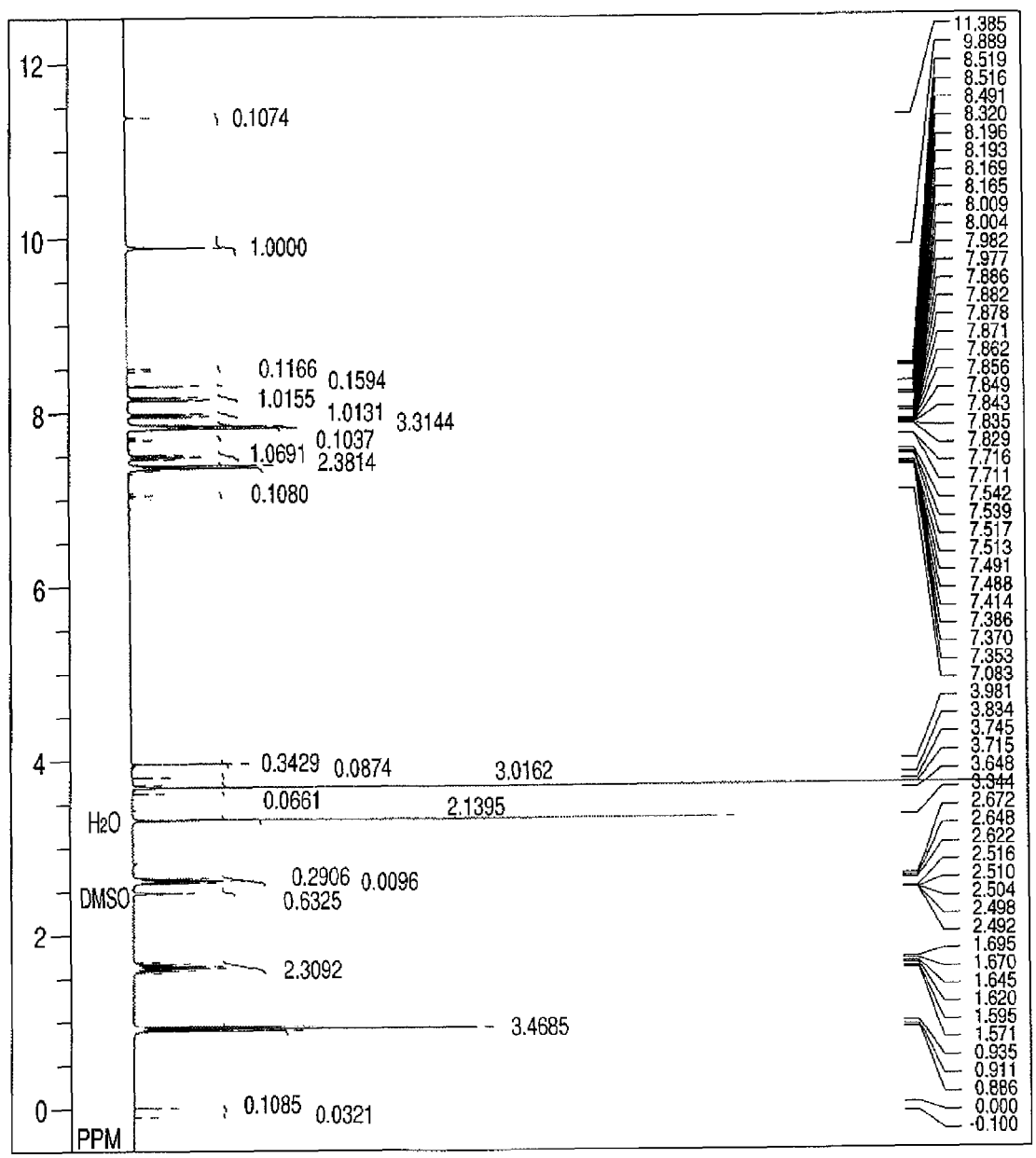
FIG. 3 illustrates the results of $^1$H-NMR measurement of the exemplified compound B-2.
Figure 4:
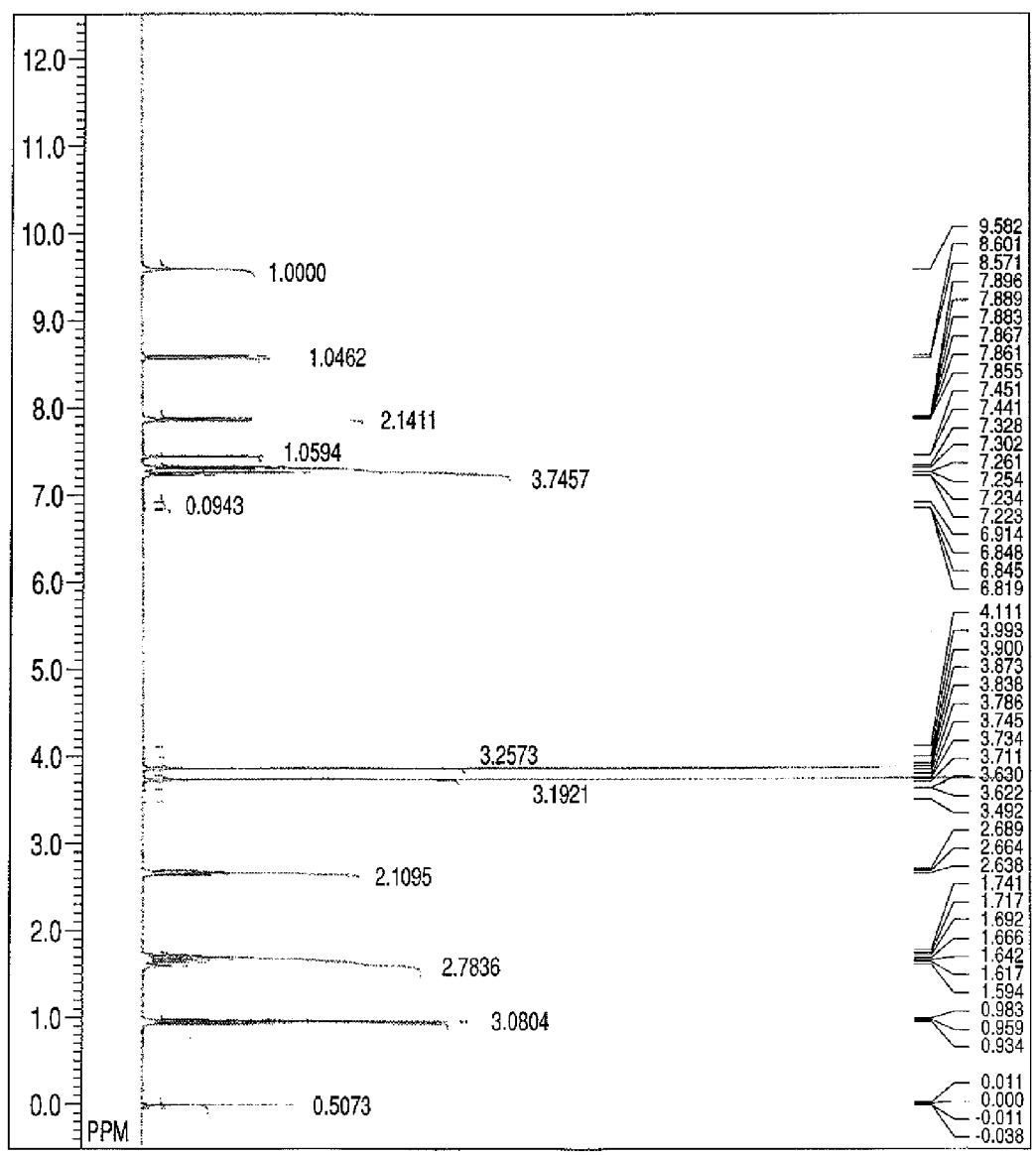
FIG. 4 illustrates the results of $^1$H-NMR measurement of the exemplified compound E-2.

The same experiment as that of Example A-2 was carried out except that the products obtained in Examples B-1 to L-1 (Exemplified Compounds B-1 to L-1) and trimethylsilyl diazomethane-hexane solution (abbreviated as "TMS diazomethane" in Tables B-1 and B-2 were used instead of Exemplified Compound A-1. The mixing ratios of the agents (unit: g, ml, or mmol) and the structures of the compounds obtained were listed in Tables B-1 and B-2, respectively. The resultant products can be confirmed by confirming a peak derived from methyl sulfonate by a $^1$H-NMR measurement. For example, the results of $^1$H-NMR measurement of B-2 are shown in FIG. 3. In addition, the results of $^1$H-NMR measurement of E-2 were shown in FIG. 4.

In addition, the preparation method was scaled up to produce 50 g of each of the compounds. Those compounds were provided as Exemplified Compounds B-2 to L-2 in Examples 1 to 40, respectively.

TABLE B-1

| Compound 2 | | Compound 1 Amount added (g) | Compound 1 Amount added (mmol) | TMS diazomethane Amount added (ml) | TMS diazomethane Amount added (mmol) |
|---|---|---|---|---|---|
| A | A-2 | 0.3 | 1.08 | 5.4 | 10.8 |

TABLE B-1-continued

| Compound 2 | | Compound 1 Amount added (g) | Compound 1 Amount added (mmol) | TMS diazomethane Amount added (ml) | TMS diazomethane Amount added (mmol) |
|---|---|---|---|---|---|
| B | B-2 | 0.4 | 1.25 | 6.3 | 12.5 |
| C | C-2 | 0.4 | 1.15 | 5.8 | 11.5 |
| D | D-2 | 0.4 | 1.25 | 6.3 | 12.5 |

TABLE B-1-continued

| Compound 2 | Compound 1 Amount added (g) | Compound 1 Amount added (mmol) | TMS diazomethane Amount added (ml) | TMS diazomethane Amount added (mmol) |
|---|---|---|---|---|
| E (E-2) | 0.4 | 1.14 | 5.7 | 11.4 |
| F (F-2) | 0.4 | 1.08 | 5.4 | 10.8 |

TABLE B-2

| Compound 2 | Compound 1 Amount added (g) | Compound 1 Amount added (mmol) | TMS diazomethane Amount added (g) | TMS diazomethane Amount added (mmol) |
|---|---|---|---|---|
| G (G-2) | 0.4 | 1.34 | 6.7 | 13.4 |
| H (H-2) | 0.3 | 1.31 | 6.5 | 13.1 |

TABLE B-2-continued

| Compound 2 | | Compound 1 Amount added (g) | Compound 1 Amount added (mmol) | TMS diazomethane Amount added (g) | TMS diazomethane Amount added (mmol) |
|---|---|---|---|---|---|
| I | I-2 | 0.4 | 1.22 | 6.1 | 12.2 |
| J | J-2 | 0.4 | 1.41 | 7.1 | 14.1 |
| K | K-2 | 0.4 | 1.22 | 6.1 | 12.2 |
| L | L-2 | 0.3 | 0.62 | 3.1 | 6.2 |

Example B-3

An aqueous solution was prepared by dissolving 50 mg (1.25 mmol) of sodium hydroxide with 10 ml of water and then added with 0.4 g (1.25 mmol) of the product obtained in Example B-1 (Exemplified Compound B-1), followed by stirring the solution for 30 min at room temperature. After completion of the reaction, water was distilled off by an evaporator. The resultant product was dried under reduced pressure, thereby obtaining 0.35 g of the product (1.03 mmol, 82% in yield). From FT-IR spectrum, any peak at about 3,200 cm$^{-1}$ derived from a sulfonic acid O—H binding was eliminated. Therefore, the product thus obtained was confirmed as a compound represented by the chemical formula (B-3) described below.

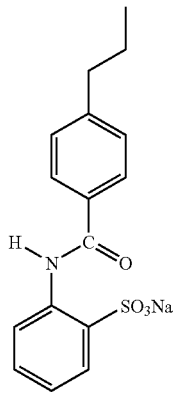

(B-3)

Example B-4

An aqueous solution was prepared by dissolving 70 mg (1.25 mmol) of potassium hydroxide with 10 ml of water and then added with 0.4 g (1.25 mmol) of the product obtained in Example B-1 (Exemplified Compound B-1), followed by stirring the solution for 30 min at room temperature. After completion of the reaction, water was distilled off by an evaporator. The resultant product was dried under reduced pressure, thereby obtaining 0.40 g of the product (1.12 mmol, 89% in yield). From FT-IR spectrum, any peak at about 3,200 $cm^{-1}$ derived from a sulfonic acid O—H binding was eliminated. Therefore, the product thus obtained was confirmed as a compound represented by the chemical formula (B-4) described below.

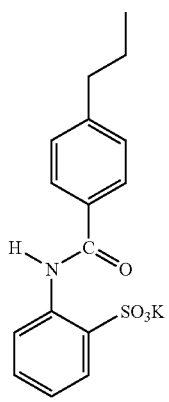

(B-4)

Example H-3

An aqueous solution was prepared by dissolving 52 mg (1.31 mmol) of sodium hydroxide with 10 ml of water and then added with 0.3 g (1.31 mmol) of the product obtained in Example H-1 (Exemplified Compound H-1), followed by stirring the solution for 30 min at room temperature. After completion of the reaction, water was distilled off by an evaporator. The resultant product was dried under reduced pressure, thereby obtaining 0.30 g of the product (1.31 mmol, 91% in yield). From FT-IR spectrum, any peak at about 3,200 $cm^{-1}$ derived from a sulfonic acid O—H binding was eliminated. Therefore, the product thus obtained was confirmed as a compound represented by the chemical formula (H-3) described below.

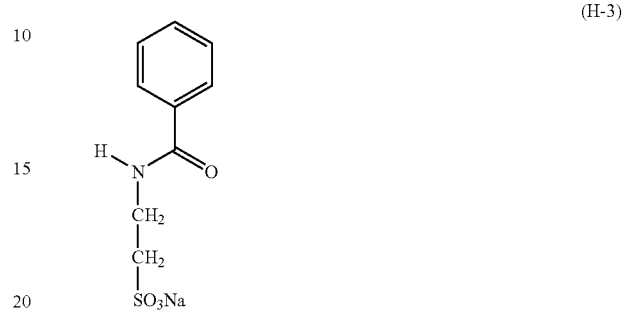

(H-3)

Next, various toners were produced by using a charge controlling agent produced by the present invention, and were evaluated.

Example 1

First, an aqueous solution of $Na_3PO_4$ was added to a 2-L four-necked flask equipped with a high-speed stirring device TK Homomixer. The number of revolutions was adjusted to 10,000 rpm, and the solution was heated to 60° C. An aqueous solution of $CaCl_2$ was gradually added to the solution to prepare an aqueous dispersion medium containing a minute and hardly water-soluble dispersant $Ca_3(PO_4)_2$. Meanwhile, the following compositions were dispersed for 3 hours by using a ball mill. Then, 10 parts by mass of a releasing agent (carnauba wax) and 10 parts by mass of 2,2'-azobis(2,4-dimethylvaleronitrile) as a polymerization initiator were added to prepare a polymerizable monomer composition.
Styrene monomer: 82 parts by mass
Ethylhexyl acrylate monomer: 18 parts by mass
Divinylbenzene monomer: 0.1 part by mass Cyan coloring agent (C.I. Pigment Blue 15): 6 parts by mass
Polyethylene oxide resin (having a molecular weight of 3,200 and an acid value of 8): 5 parts by mass
Exemplified Compound A-1: 2 parts by mass Next, the polymerizable monomer composition thus obtained was charged into the aqueous dispersion medium prepared in advance, and the whole was granulated while the number of revolutions was kept at 10,000 rpm. After that, the resultant was allowed to react at 65° C. for 3 hours while being stirred with a paddle stirring blade. Then, the resultant was polymerized at 80° C. for 6 hours to complete the polymerization reaction. After the completion of the reaction, the suspension was cooled, and an acid was added to dissolve the hardly water-soluble dispersant $Ca_3(PO_4)_2$. Then, the resultant was filtered, washed with water, and dried to yield blue polymerized particles (1). The grain size of the resultant blue polymerized particles (1) was measured by means of a Coulter Counter Multisizer (manufactured by Coulter). The particles had a weight average particle size of 7.5 μm and a fine powder amount (an abundance ratio of particles each having a particle size of 3.17 μm or less in a number distribution) of 5.1 number %.

1.3 parts by mass of hydrophobic silica fine powder treated with hexamethyldisilazane (BET: 270 $m^2/g$) as a fluidity improver were dry-mixed with and externally added to 100 parts by mass of the blue polymerized particles (1) thus prepared by using a Henschel mixer, to thereby produce a blue toner (1) of this example. Further, 7 parts by mass of the blue toner (1) and 93 parts by mass of a resin-coated magnetic ferrite carrier (average particle size: 45 μm) were mixed to prepare a two-component blue developer (1) for magnetic brush development.

Examples 2 to 5

Each of blue toners (2) to (5) of Examples 2 to 5 was produced in the same manner as in Example 1 except that Exemplified Compound A-1 was changed to any one of Exemplified Compounds D-2, N-1, F-1; and H-3. The properties of the toners were measured in the same manner as in Example 1. Table 1 shows the results. In addition, the toners were used to prepare two-component blue developers (2) to (5) of Examples 2 to 5 in the same manner as in Example 1.

Comparative Example 1

A blue toner (6) of Comparative Example 1 was produced in the same manner as in Example 1 except that Exemplified Compound A-1 was not used. The properties of the toner were measured in the same manner as in Example 1. Table 1 shows the results. In addition, the toner was used to prepare a two-component blue developer (6) of Comparative Example 1 in the same manner as in Example 1.

Examples 6 to 10

Each of yellow toners (1) to (5) of Examples 6 to 10 was produced in the same manner as in Example 1 except that: 2.0 parts by mass of each of Exemplified Compounds M-1, D-1, I-1, B-2, and H-2 were used instead of Exemplified Compound A-1; and a yellow coloring agent (Hansa yellow G) was used instead of the cyan coloring agent. The properties of the toners were measured in the same manner as in Example 1. Table 1 shows the results. In addition, the toners were used to prepare two-component yellow developers (1) to (5) in the same manner as in Example 1.

Comparative Example 2

A yellow toner (6) of Comparative Example 2 was produced in the same manner as in Example 1 except that: Exemplified Compound A-1 was not used; and a yellow coloring agent (Hansa yellow G) was used instead of the cyan coloring agent. The properties of the toner were measured in the same manner as in Example 1. Table 1 shows the results. In additions the toner was used to prepare a two-component yellow developer (6) of Comparative Example 2 in the same manner as in Example 1.

Examples 11 to 15

Each of black toners (1) to (5) of Examples 11 to 15 was produced in the same manner as in Example 1 except that: 2.0 parts by mass of each of Exemplified Compounds H-1, K-2, B-1, O-1, and G-2 were used instead of Exemplified Compound A-1; and carbon black (DBP oil absorption 110 mL/100 g) was used instead of the cyan coloring agent. The properties of the toners were measured in the same manner as in Example 1. Table 1 shows the results. In addition, the toners were used to prepare two-component black developers (1) to (5) in the same manner as in Example 1.

Comparative Example 3

A black toner (6) of Comparative Example 3 was produced in the same manner as in Example 1 except that: Exemplified Compound A-1 was not used; and carbon black (DBP oil absorption 110 mL/100 g) was used instead of the cyan coloring agent. The properties of the toner were measured in the same manner as in Example 1. Table 1 shows the results. In addition, the toner was used to prepare a two-component black developer (6) of Comparative Example 3 in the same manner as in Example 1.

Example 16

Styrene-butyl acrylate copolymer resin (having a glass transition temperature of 70° C.): 100 parts by mass
Wax (low-molecular weight polyethylene, having a melting point of 94° C.): 7 parts by mass
Magenta pigment (C.I. Pigment Red 114): 5 parts by mass
Exemplified Compound J-2: 2 parts by mass The above-mentioned compositions were mixed, and the mixture was melted and kneaded by means of a biaxial extruder (L/D=30). The kneaded product was cooled, roughly pulverized by means of a hammer mill, and finely pulverized by means of a jet mill. After that, the finely pulverized product was classified to yield magenta colored particles (1). The grain size of the magenta colored particles (1) was measured. The particles had a weight average particle size of 7.3 μm and a fine powder amount of 5.0 number %.

1.5 parts by mass of hydrophobic silica fine powder treated with hexamethyldisilazane (BET: 250 m$^2$/g) as a fluidity improver were dry-mixed with 100 parts by mass of the magenta colored particles (1) by using a Henschel mixer, to thereby produce a magenta toner (1) of this example. Further 7 parts by mass of the resultant magenta toner (1) and 93 parts by mass of a resin-coated magnetic ferrite carrier (average particle size: 45 μm) were mixed to prepare a two-component magenta developer (1) for magnetic brush development.

Examples 17 to 20

Each of magenta toners (2) to (5) of Examples 17 to 20 was produced in the same manner as in Example 16 except that Exemplified Compound J-2 was changed to any one of Exemplified Compounds E-1, A-2, L-1, and B-3. The properties of the toners were measured in the same manner as in Example 1. Table 1 shows the results. In addition, the toners were used to prepare two-component magenta developers (2) to (5) of Examples 17 to 20 in the same manner as in Example 16.

Comparative Example 4

A magenta toner (6) of Comparative Example 4 was produced in the same manner as in Example 16 except that Exemplified Compound J-2 was not used. The properties of the toner were measured in the same manner as in Example 1. Table 1 shows the results. In addition, the toner was used to prepare a two-component magenta developer (6) of Comparative Example 4 in the same manner as in Example 16.

Examples 21 to 25

Each of black toners (7) to (11) of Examples 21 to 25 was produced in the same manner as in Example 16 except that: 2.0 parts by mass of each of Exemplified Compounds C-1, I-2, J-1, L-2, and E-2 were used instead of Exemplified Compound J-2; and carbon black (DBP oil absorption 110 mL/100 g) was used instead of the magenta pigment. The properties of the toners were measured in the same manner as in Example 1. Table 1 shows the results. In addition, the toners were used to prepare two-component black developers (7) to (11) in the same manner as in Example 16.

Comparative Example 5

A black toner (12) of Comparative Example 5 was produced in the same manner as in Example 16 except that: Exemplified Compound J-2 was not used; and carbon black (DBP oil absorption 110 mL/100 g) was used instead of the magenta pigment. The properties of the toner were measured in the same manner as in Example 1. Table 1 shows the results. In addition, the toner was used to prepare a two-component black developer (12) of Comparative Example 5 in the same manner as in Example 16.

Example 26

Polyester resin: 100 parts by mass
Carbon black (DBP oil absorption 110 mL/100 g): 5 parts by mass
Exemplified Compound G-1: 2 parts by mass The polyester resin was synthesized as follows. 751 parts of bisphenol A propylene oxide 2 mole adduct, 104 parts of terephthalic acid, and 167 parts of trimellitic anhydride were subjected to polycondensation by using 2 parts of dibutyltin oxide as a catalyst to produce the polyester resin having a softening point of 125° C.

The above-mentioned compositions were mixed, and the mixture was melted and kneaded by means of a biaxial extruder (L/D=30). The kneaded product was cooled, roughly pulverized by means of a hammer mill, and finely pulverized by means of a jet mill. After that, the finely pulverized product was classified to yield black colored particles (13). The grain size of the black colored particles (13) was measured. The particles had a weight average particle size of 7.7 μm and a fine powder amount of 5.2 number %.

1.5 parts by mass of hydrophobic silica fine powder treated with hexamethyldisilazane (BET: 250 m²/g) as a fluidity improver were dry-mixed with 100 parts by mass of the black colored particles (13) by using a Henschel mixer, to thereby produce a black toner (13) of this example. Further, 7 parts by mass of the resultant black toner (13) and 93 parts by mass of a resin-coated magnetic ferrite carrier (average particle size: 45 μm) were mixed to prepare a two-component black developer (13) for magnetic brush development.

Examples 27 to 30

Each of black toners (14) to (17) of Examples 27 to 30 was produced in the same manner as in Example 26 except that Exemplified Compound G-1 was changed to any one of Exemplified Compounds C-2, K-1, F-2, and B-4. The properties of the toners were measured in the same manner as in Example 1. Table 1 shows the results. In addition, the toners were used to prepare two-component black developers (14) to (17) of Examples 27 to 30 in the same manner as in Example 26.

Comparative Example 6

A black toner (18) of Comparative Example 6 was produced in the same manner as in Example 26 except that Exemplified Compound G-1 was not used. The properties of the toner were measured in the same manner as in Example 1. Table 1 shows the results. In addition, the toner was used to prepare a two-component black developer (18) of Comparative Example 6 in the same manner as in Example 26.

<Evaluation>

The two-component developers obtained in Examples 1 to 30 described above and two-component developers obtained in Comparative Examples 1 to 6 were evaluated, respectively. To be specific, a charge amount measuring device shown in FIG. 5 was used for the measurement.

First, in a constant environment, an EFV 200/300 (manufactured by Powder Tech) is used as a carrier. Subsequently, a mixture obtained by the addition of 0.5 g of toner as a target of the measurement to 9.5 g of the carrier is placed in a polyethylene bottle of 50 to 100 ml, in volume. The bottle is set in a shaker with constant amplitude and then shaken for a predetermined period of time under shaking conditions of: an amplitude of 100 mm; and a shaking speed of 100 reciprocations/min. Next, 1.0 to 1.2 g of the mixture is placed in a metallic measurement container 42, which has a 500 mesh screen 43 at its bottom, of a charge amount measuring device 41 shown in FIG. 5. Then, the container is capped with a metallic cap 44. The mass of the entire measurement container 42 at this time is measured and designated by W1 (g) Next, the toner in the container is sucked through a suction port 47 by means of a sucker (not shown) (at least part of the sucker in contact with the measurement container 42 is made of an insulator), and an air quantity regulating valve 46 is adjusted in such a manner that a vacuum gage 45 indicates a pressure of 2,450 Pa (250 mmAq). Suction is performed for 1 min in this state to suck and remove the toner. The potential of a potentiometer 49 at this time is designated by V (volt). Here, reference numeral 48 denotes a capacitor having a capacity of C (μF). In addition, the mass of the entire measuring device after the suction is measured and designated by W2 (g). The frictional charge amount of the toner (μC/g) is calculated from those measured values according to the following equation.

$$\text{Frictional charge amount } (\mu C/g) = C \times V/(W1-W2) \quad \text{Equation:}$$

Toner charge amounts 10 sec and 300 sec after stirring in a normal-temperature-and-normal-humidity (25° C., 60% RH) environment and a high-temperature-and-high-humidity (30° C., 80% RH) environment were measured by means of the method of measuring a charge amount described above. Then, the measured value of a two-component blow-off charge amount was rounded to one decimal place, and the resultant value was evaluated according to the following criteria. Table 1 summarizes the results.

(Chargeability)
AA: Very good (−20 μC/g or less)
A: Good (−19.9 to −10.0 μC/g)
B: Practicable (−9.9 to −5.0 μC/g)
C: Not practicable (−4.9 μC/g or more)

TABLE 1

| Example | Exemplified Compound No. | Toner No. | Particle size distribution Average particle size (μm) | Particle size distribution Fine powder amount (%) | Chargeability Normal temperature and normal humidity (Q/M) 10 Sec | Chargeability Normal temperature and normal humidity (Q/M) 300 Sec | Chargeability High temperature and high humidity (Q/M) 10 Sec | Chargeability High temperature and high humidity (Q/M) 300 Sec |
|---|---|---|---|---|---|---|---|---|
| 1 | A-1 | Blue 1 | 7.5 | 5.5 | AA | AA | AA | AA |
| 2 | D-2 | Blue 2 | 7.3 | 5.3 | AA | AA | AA | AA |
| 3 | N-1 | Blue 3 | 7.1 | 5.1 | AA | AA | AA | AA |
| 4 | F-1 | Blue 4 | 7.3 | 5.4 | AA | AA | AA | AA |
| 5 | H-3 | Blue 5 | 7.0 | 5.8 | AA | AA | AA | AA |
| 6 | M-1 | Yellow 1 | 7.4 | 5.5 | AA | AA | AA | AA |
| 7 | D-1 | Yellow 2 | 7.1 | 5.6 | AA | AA | AA | AA |
| 8 | I-1 | Yellow 3 | 7.2 | 5.0 | AA | AA | AA | AA |
| 9 | B-2 | Yellow 4 | 7.0 | 5.5 | AA | AA | AA | AA |
| 10 | H-2 | Yellow 5 | 7.5 | 5.5 | AA | AA | AA | AA |
| 11 | H-1 | Black 1 | 7.7 | 5.5 | AA | AA | AA | AA |
| 12 | K-2 | Black 2 | 7.4 | 5.2 | AA | AA | AA | AA |
| 13 | B-1 | Black 3 | 7.3 | 5.4 | AA | AA | AA | AA |
| 14 | O-1 | Black 4 | 7.1 | 5.7 | AA | AA | AA | AA |
| 15 | G-2 | Black 5 | 7.4 | 5.2 | AA | AA | AA | AA |
| 16 | J-2 | Magenta 1 | 7.3 | 5.0 | AA | AA | AA | AA |
| 17 | E-1 | Magenta 2 | 7.3 | 5.3 | AA | AA | AA | AA |
| 18 | A-2 | Magenta 3 | 7.4 | 4.8 | AA | AA | AA | AA |
| 19 | L-1 | Magenta 4 | 7.5 | 4.9 | AA | AA | AA | AA |
| 20 | B-3 | Magenta 5 | 6.9 | 5.1 | AA | AA | AA | AA |
| 21 | C-1 | Black 7 | 7.6 | 5.6 | AA | AA | AA | AA |
| 22 | I-2 | Black 8 | 7.2 | 5.2 | AA | AA | AA | AA |
| 23 | J-1 | Black 9 | 7.4 | 5.3 | AA | AA | AA | AA |
| 24 | L-2 | Black 10 | 7.6 | 5.7 | AA | AA | AA | AA |
| 25 | E-2 | Black 11 | 7.0 | 5.1 | AA | AA | AA | AA |
| 26 | G-1 | Black 13 | 7.7 | 5.2 | AA | AA | AA | AA |
| 27 | C-2 | Black 14 | 7.2 | 5.4 | AA | AA | AA | AA |
| 28 | K-1 | Black 15 | 7.3 | 5.0 | AA | AA | AA | AA |
| 29 | F-2 | Black 16 | 7.6 | 5.6 | AA | AA | AA | AA |
| 30 | B-4 | Black 17 | 7.6 | 5.5 | AA | AA | AA | AA |
| Comparative example 1 | | Blue 6 | 7.3 | 5.5 | C | B | C | C |
| Comparative example 2 | | Yellow 6 | 7.0 | 5.5 | C | C | C | C |
| Comparative example 3 | | Black 6 | 7.0 | 4.9 | C | B | C | B |
| Comparative example 4 | | Magenta 6 | 7.1 | 5.0 | C | B | C | C |
| Comparative example 5 | | Black 12 | 7.2 | 5.3 | C | C | C | C |
| Comparative example 6 | | Black 18 | 5.2 | 6.8 | C | C | C | C |

Examples 31 to 36 and Comparative Examples 7 to 12

In Examples 31 to 36 and Comparative Examples 7 to 12, evaluation was performed using a printer, a modified version of LBP-5500 (manufactured by Canon Inc.).

In this case, a toner image was formed using a cyan toner, an yellow toner, a magenta toner, and a black toner, which were obtained as developers in Examples 1, 6, 11, 16, 21, and 26 and Comparative Examples 1 to 6.

<Evaluation>

Under the above-mentioned conditions, a print out test was performed by the LBP-5500 printer modified to attain a printing-out rate of 8 sheets (A4 size)/min in a normal-temperature-and-normal-humidity (25° C., 60% RH) environment and a high-temperature-and-high-humidity (30° C., 80% RH) environment.

Toners of Examples 1, 6, 11, 16, 21, and 26 and toners of Comparative Examples 1 to 6 were respectively used for successively supplying the toners to carry out a print-out test in a monochrome intermittent mode. The resultant printed-out images were evaluated on the basis of the following items.

Here the term "intermittent mode" refers to a mode in which a developing unit is suspended for 10 sec each time one sheet is printed out, and deterioration of toner is accelerated by a preliminary operation at the time of restart.

Evaluation results are listed in Table 2.

(Printed-Out Image Evaluation)

1. Image Density

Print out of a predetermined number of sheets of ordinary plain paper for a copying machine (75 g/m$^2$) was performed. An image density was evaluated according to the degree to which an image maintained its image density at the time of completion of printing as compared to an initial image. The relative density of a white portion having an original density of 0.00 with respect to a printed-out image was measured by using a Macbeth reflection densitometer (manufactured by Macbeth), and was used for evaluation.

AA: Excellent (An image density at the time of completion is 1.40 or more.)

A: Good (An image density at the time of completion is 1.35 or more and less than 1.40.)

B: Acceptable (An image density at the time of completion is 1.00 or more and less than 1.35.)

C: Not acceptable (An image density at the time of completion is less than 1.00.)

2. Image Fogging

Print out of predetermined number of sheets of ordinary plain paper for a copying machine (75 g/m$^2$) was performed. A solid white image at the time of completion of printing was evaluated for image fogging. To be specific, the image was evaluated for image fogging by means of the following method. The low value of a white portion reflection density after printing and an average reflection density of paper before printing measured by using a reflection densitometer (manufactured by TOKYO DENSHOKU CO., LTD, REFLECTOMETER MODEL TC-6DS) were denoted by Ds and Dr, respectively, and (Ds−Dr) was determined from those values. The resultant value used was defined as a fogging amount, and was evaluated according to the following criteria.

AA: Very good (A fogging amount is 0% or more and less than 1.5%.)
A: Good (A fogging amount is 1.5% or more and less than 3.0%.)
B: Practicable (A fogging amount is 3.0% or more and less than 5.0%.)
C: Not practicable (A fogging amount is 5.0% or more.)

3. Transferability

Solid black images were printed out on a predetermined number of sheets of ordinary plain paper for a copying machine (75 g/m$^2$). The image omission amount of an image at the time of completion of printing was visually observed, and was evaluated according to the following criteria.

AA: Very good (Nearly no omission occurs)
A: Good (Omission slightly occurs)
B: Practicable
C: Not practicable In addition, in each of Examples 31 to 36 and Comparative Examples 7 to 12, the states of occurrence of: flaws on the surfaces of the photosensitive drum and the intermediate transfer member; and adherence of residual toner to the surfaces, and influences of the flaws and the residual toner on a printed-out image (matching with LBP 5500) when 5,000 images were output were visually evaluated.

In a system using each of the toners of Examples 31 to 36, neither flaw on the surfaces of the photosensitive drum and the intermediate transfer member nor adherence of the toner to the surfaces was observed, so matching with LBP 5500 was very good. On the other hand, in a system using each of the toners of Comparative Examples 7 to 12, adherence of the toner to the surface of the photosensitive drum was observed. Further, in the system using each of the toners of Comparative Examples 7 to 12, adherence of the toner to the surface of the intermediate transfer member and a flaw on the surface were observed, and a vertical stripe-like image defect on an image occurred.

|  |  | Normal temperature and normal humidity | | | High temperature and high humidity | | |
| --- | --- | --- | --- | --- | --- | --- | --- |
| Example | Toner number | Image density | Image fogging | Transferability | Image density | Image fogging | Transferability |
| 31 | Blue 1 | AA | AA | AA | AA | AA | AA |
| 32 | Yellow 1 | AA | AA | AA | AA | AA | AA |
| 33 | Black 1 | AA | AA | AA | AA | AA | AA |
| 34 | Magenta 1 | AA | AA | AA | AA | AA | AA |
| 35 | Black 7 | AA | AA | AA | AA | AA | AA |
| 36 | Black 13 | AA | AA | AA | AA | AA | AA |
| Comparative example 7 | Blue 6 | C | C | C | C | C | C |
| Comparative example 8 | Yellow 6 | C | C | C | C | C | C |
| Comparative example 9 | Black 6 | B | B | C | B | C | C |
| Comparative example 10 | Magenta 6 | B | B | C | B | C | C |
| Comparative example 11 | Black 12 | B | B | C | C | C | C |
| Comparative example 12 | Black 18 | B | B | C | B | C | C |

Examples 37 to 39 and Comparative Examples 13 to 15

In performing each of Examples 37 to 39 and Comparative Examples 13 to 15, each of the toners produced in Examples 1, 6, and 11 and Comparative Examples 1 to 3 was used as a developer. Used as means for forming an image was an image forming apparatus reconstructed and reset by providing a reuse mechanism (system for reusing a collected toner) for LBP 5500.

Under the above-mentioned conditions, print out of up to 30,000 sheets was performed in a continuous mode in a normal-temperature-and-normal-humidity (25° C., 60% RH) environment at a print out rate of 8 sheets (A4 size)/min while toner was sequentially supplied. The image density of the resultant printed-out image was measured, and the image was evaluated for durability according to the following criteria. In addition, a 10,000th image was observed and evaluated for image fogging according to the following criteria. At the same time, the state of each device constituting LBP 5500 after the duration test was observed to evaluate matching between each device and each of the above-mentioned toners. Table 3 summarizes the results of the evaluation. Note that, the continuous mode is a mode in which deterioration of toner is accelerated without the suspension of a developing unit.

(Transition of Image Density at the Time of Duration)

Print out of a predetermined number of sheets of ordinary plain paper for a copying machine (75 g/m$^2$) was performed. An image density was evaluated according to the degree to which an image maintained its image density at the time of completion of printing as compared to an initial image. The relative density of a white portion having an original density of 0.00 with respect to a printed-out image was measured by using a Macbeth reflection densitometer (manufactured by Macbeth), and was used for evaluation.

AA: Excellent (An image density at the time of completion is 1.40 or more.)
A: Good (An image density at the time of completion is 1.35 or more and less than 1.40.)
B: Acceptable (An image density at the time of completion is 1.00 or more and less than 1.35.)
C: Not acceptable (An image density at the time of completion is less than 1.00.)

(Image Fogging)

Print out of a predetermined number of sheets of ordinary plain paper for a copying machine (75 g/m²) was performed. A solid white image at the time of completion of printing was evaluated for image fogging. The evaluation was performed by the method using a reflection densitometer (manufactured by TOKYO DENSHOKU CO., LTD, REFLECTOMETER MODEL TC-6DS) as described above.

(Image Forming Apparatus Matching Evaluation)

1. Matching with Developing Sleeve

After the completion of the print out test, the state where residual toner adhered to the surface of a developing sleeve and an influence of the residual toner on a printed-out image were visually evaluated.
AA: Very good (No adherence occurs.)
A: Good (Nearly no adherence occurs.)
B: Practicable (Adherence occurs, but affects an image little.)
C: Not practicable (Adherence is remarkable, and causes image unevenness.)

2. Matching with Photosensitive Drum

The states of occurrence of: a flaw on the surface of a photosensitive drum; and adherence of residual toner to the surface, and influences of the flaw and the residual toner on a printed-out image were visually evaluated.
AA: Very good (Neither flaw nor adherence occurs.)
A: Good (R slight flaw occurs, but does not affect an image.)
B: Practicable (Adherence and a flaw occur, but affect an image little.)
C: Not practicable (Adherence is remarkable, and causes a vertical stripe-like image defect.)

3. Matching with Fixing Device

The state of a fixation film surface was observed, and results of surface property and the state of adherence of residual toner were generally averaged to evaluate the surface for durability.

(1) Surface Property

The states of occurrence of a flaw or shaving on the surface of a fixation film after the completion of the print out test were visually observed and evaluated.
AA: Very good (No occurrence)
A: Good (Nearly no occurrence)
B: Practicable
C: Not practicable (2) State of Adherence of Residual Toner The state of adherence of residual toner on the surface of a fixation film after the completion of the print out test was visually observed and evaluated.
AA: Very good (No occurrence)
A: Good (Nearly no occurrence)
B: Practicable
C: Not practicable

| | | Printed-out image evaluation | | | | Evaluation of matching with each device | | | |
| | | Transition of image density at the time of duration | | | Image fogging | Develop- | Photo- | Fixing device | |
| Example | Toner | Initial | 1,000 sheets | 10,000 sheets | 30,000 sheets | 10,000 sheets | ing sleeve | sensitive drum | Surface property | Toner adherence |
|---|---|---|---|---|---|---|---|---|---|---|
| 37 | Blue 1 | AA | AA | AA | AA | AA | AA | AA | AA | AA |
| 38 | Yellow 1 | AA | AA | AA | AA | AA | AA | AA | AA | AA |
| 39 | Black 1 | AA | AA | AA | AA | AA | AA | AA | AA | AA |
| Comparative example 13 | Blue 6 | B | C | C | C | C | C | C | C | C |
| Comparative example 14 | Yellow 6 | B | C | C | C | C | C | C | C | C |
| Comparative example 15 | Black 6 | A | B | C | C | C | C | C | C | C |

Example 40

A print out test was performed in the same manner as in Example 37 except that: the toner reuse mechanism of LBP 5500 used in Examples 37 to 39 and Comparative Examples 13 to 15 was removed; and the print out rate was changed to 16 sheets (A4 size)/min.

The print out test was performed in a continuous mode (that is, a mode in which consumption of toner is accelerated without the suspension of a developing unit) while the blue toner (1) of Example 1 was sequentially supplied. The resultant printed-out image and matching with LBP 5500 were evaluated for the same items as those of Examples 37 to 39 and Comparative Examples 13 to 15. As a result, good results were obtained for all of the items.

While the present invention has been described with reference to exemplary embodiments, it is to be understood that the present invention is not limited to the disclosed exemplary embodiments. The scope of the following claims is to be accorded the broadest interpretation so as to encompass all such modifications and equivalent structures and functions.

This application claims the benefit of Japanese Patent Application No. 2005-328210, filed Nov. 11, 2005, which is hereby incorporated by reference herein in its entirety.

What is claimed is:
1. A toner for developing an electrostatic charge, image comprising:
a binder resin;
a coloring agent; and
a compound represented by the chemical formula (2):

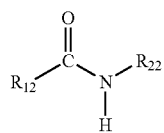 (2)

wherein $R_{12}$ and $R_{22}$ satisfy the following conditions (1) to (4);

(1) $R_{12}$ and $R_{22}$ independently represent any one of a substituted or unsubstituted aliphatic hydrocarbon structure, a substituted or unsubstituted aromatic ring structure, or a substituted or unsubstituted heterocyclic structure;

(2) at least one of $R_{12}$ and $R_{22}$ contains at least one $SO_2R_{32}$ group as a substituent;

(3) $R_{32}$ is $OR_{42}$; and (4) $R_{42}$ represents any one of a substituted or unsubstituted aliphatic hydrocarbon structure, a substituted or unsubstituted aromatic ring structure, or a substituted or unsubstituted heterocyclic structure.

* * * * *